(12) United States Patent
Mohan

(10) Patent No.: US 11,009,507 B2
(45) Date of Patent: May 18, 2021

(54) METHODS AND DIAGNOSTICS FOR CANCER DETECTION AND TREATMENT MONITORING

(71) Applicant: University of New England, Biddeford, ME (US)

(72) Inventor: Srinidi Mohan, Biddeford, ME (US)

(73) Assignee: University of New England, Biddeford, ME (US)

( * ) Notice: Subject to any disclaimer, the term of this patent is extended or adjusted under 35 U.S.C. 154(b) by 0 days.

(21) Appl. No.: 16/570,747

(22) Filed: Sep. 13, 2019

(65) Prior Publication Data

US 2020/0141938 A1 May 7, 2020

Related U.S. Application Data

(60) Provisional application No. 62/840,581, filed on Apr. 30, 2019, provisional application No. 62/754,053, filed on Nov. 1, 2018, provisional application No. 62/731,269, filed on Sep. 14, 2018.

(51) Int. Cl.
*C07K 1/00* (2006.01)
*G01N 33/574* (2006.01)
*C07K 14/47* (2006.01)

(52) U.S. Cl.
CPC ..... *G01N 33/57415* (2013.01); *C07K 14/4748* (2013.01); *G01N 33/57449* (2013.01); *C07K 2317/565* (2013.01)

(58) Field of Classification Search
CPC .......................... G01N 33/57415; C07K 1/00
USPC ....................................................... 435/7.23
See application file for complete search history.

(56) References Cited

U.S. PATENT DOCUMENTS 10,073,099 B2  9/2018  Mohan
2007/0041978 A1  2/2007  Hattori et al.

2008/0052007 A1  2/2008  Yu et al.
2011/0039788 A1  2/2011  Briegel
2012/0046199 A1  2/2012  Ruijtenbeek et al.
2017/0089902 A1  3/2017  Mohan
2018/0356422 A1  12/2018  Mohan

FOREIGN PATENT DOCUMENTS

WO  2017053535 A1  3/2017
WO  2020056334 A1  3/2020

OTHER PUBLICATIONS

Rudikoff et al. (Proceedings of the National Academy of Sciences, 1982, 79:1979-1983).*
MacCallum et al. (Journal of Molecular Biology, 1996, 262:732-745).*
Mohan et al., "N w-hydroxy-L-arginine as a novel ethnic specific indicator of estrogen-negative breast cancer," Amino Acids, Aug. 9, 2016, vol. 48, pp. 2693-2698.
Mohan et al., "Metabolic relevance for N-hydroxy L-arginine reduction in estrogen-negative breast cancer cells," Amino Acids, ePub Jun. 20, 2018, vol. 50, No. 11, pp. 1629-1636.
Pervin et al., "Nitric oxide, N omega-hydroxy-L-arginine and breast cancer," Nitric Oxide, Apr. 24, 2008, vol. 19, pp. 103-106.
Pow et al., "Immunocytochemical analysis of the transport of arginine analogues into nitrergic neurons and other cells in the retina and pituitary," Cell & Tissue Research, Feb. 15, 1997, vol. 290, pp. 501-514.
Singh et al., "Proteomic identification of mitochondrial targets of arginase in human breast cancer," PLoS One, Nov. 5, 2012, vol. 8, e79242, pp. 1-15.
PCT International Search Report in International Patent Application No. PCT/US2019/051124 dated Feb. 19, 2020.

* cited by examiner

*Primary Examiner* — Sean E Aeder
(74) *Attorney, Agent, or Firm* — Greenberg Traurig, LLP; Roman Fayerberg

(57) ABSTRACT

Provided herein are methods and compositions for detecting and characterizing estrogen receptor-negative solid tumor cancers.

11 Claims, 13 Drawing Sheets

Specification includes a Sequence Listing.

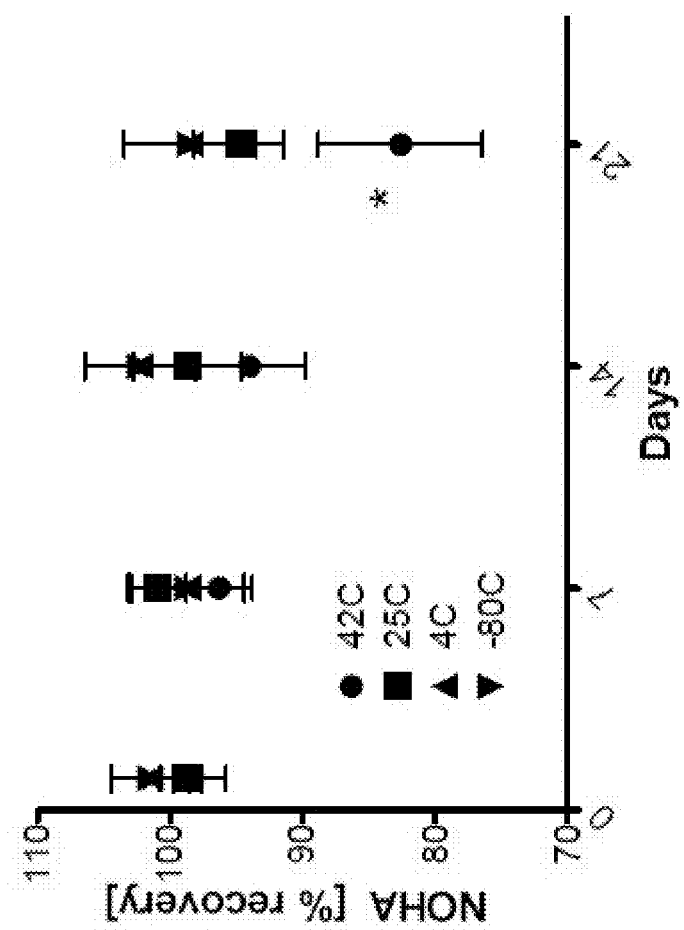

METHODS AND DIAGNOSTICS FOR CANCER DETECTION AND TREATMENT MONITORING

CROSS-REFERENCE TO RELATED APPLICATION

This application claims the benefit of and priority to U.S. Provisional Application Nos. 62/731,269, filed Sep. 14, 2018; 62/754,053, filed Nov. 1, 2018; and 62/840,581, filed Apr. 30, 2019, the entire contents of each of which are incorporated herein by reference.

SEQUENCE LISTING

The instant application contains a Sequence Listing that has been submitted electronically in ASCII format and is hereby incorporated by reference in its entirety. Said ASCII copy, created on Jan. 24, 2020, is named "162234.010303US_SL.txt" and is 16,262 bytes in size.

FIELD

The present disclosure provides methods for diagnosing breast and ovarian cancers (e.g., tumors) and monitoring treatments of breast and ovarian cancers, as well as compositions and kits that can be used in such methods.

BACKGROUND

Breast cancer and ovarian cancer are common types of cancer that result in thousands of deaths in women in the United States every year. Both cancers are solid tumor cancers that can be characterized as estrogen receptor-negative (ER−) and ER-positive (ER+) tumors. The ER− subtype is the more aggressive subtype, and cancers or tumors characterized as ER− are more difficult to treat. The ER− subtypes is also characterized by greater ethnic disparity, worse prognosis, and almost twice the risk of mortality than ER+ tumors. There is an urgent need to identify novel indicators for ER− breast cancer and ovarian cancer prognosis.

SUMMARY

Methods and diagnostic compositions for monitoring ER− breast and ovarian cancer are disclosed.

In one aspect, a method is provided for detecting an ER− tumor in a subject having or suspected of having cancer, the method involves contacting a sample derived from the subject with an antibody, or an antigen-binding fragment thereof, that specifically binds N$^{\omega}$-hydroxy-L-Arginine (NOHA), and detecting binding between NOHA and the NOHA antibody or the antigen-binding fragment thereof. In some embodiments, the method further involves determining the amount of NOHA present in the sample, wherein a reduced amount of NOHA in the sample compared to a control sample or a reference amount of NOHA is indicative of ER− cancer. In some embodiments, the ER− cancer is breast cancer or ovarian cancer.

Another aspect provides a method of monitoring breast cancer or ovarian cancer in a subject involving contacting a first and a second sample derived from the subject with an antibody or an antigen-binding fragment thereof that specifically binds N$^{\omega}$-hydroxy-L-Arginine (NOHA), wherein the second sample is obtained from the subject subsequent to when the first sample is obtained from the subject; detecting binding of NOHA to the antibody or the antigen-binding fragment thereof in the first and second samples, and comparing the detected binding in the first and second samples, wherein a change in the amount of NOHA in the second sample relative to the first is indicative of change in disease status in the subject.

In some embodiments of the methods presented herein, the detecting is by immunoassay. In some embodiments, In some embodiments, the antibody or antigen binding fragment includes at least three complementarity determining regions (CDRs), wherein the CDRs include: polypeptides comprising the amino acid sequences SGYYWN (SEQ ID NO:14), YTNYDGSNNYNPSLKN (SEQ ID NO:16), and PYLDY (SEQ ID NO:18), polypeptides comprising the amino acid sequences SNVMH (SEQ ID NO:30), YINPYNDGTKYNEKFKG (SEQ ID NO:32), and HFDYYGRGYAVDY (SEQ ID NO:34), polypeptides comprising the amino acid sequences SVSSSISSSYLH (SEQ ID NO:46) GTSNLAS (SEQ ID NO:48), and QQWSSYPLT (SEQ ID NO:50), or polypeptides comprising the amino acid sequences SASQDISNYLN (SEQ ID NO:62), YTSSLHS (SEQ ID NO:64), and LQYSKLPWT (SEQ ID NO:66). In some embodiments, the antibody or antigen fragment thereof includes the following CDRs: SGYYWN (SEQ ID NO:14), YTNYDGSNNYNPSLKN (SEQ ID NO:16), PYLDY (SEQ ID NO:18), SVSSSISSSYLH (SEQ ID NO:46) GTSNLAS (SEQ ID NO:48), and QQWSSYPLT (SEQ ID NO:50). In some embodiments, the antibody or antigen fragment thereof includes at least one polypeptide having an amino acid sequence having at least 90% sequence identity to MMVLSLLYLLTAIPG-ILSDVQLQESGPGLVKP-SQSLSLTCSVTGYSITSGYYWNWIRQFPGNKLE WMGYTNYDGSNNYNPSLKNRISITRDTSKNQF-FLKLNSVTTEDTGTYYCAGPYLDYWGQGTTL TVSS (SEQ ID NO:6); MEWSGIFLFLLSGTAGVHFE-VQLQQSGPELVKPGASVKMSCK-ASGYKFTSNVMHWVKQKPGQ GLEWIGY-INPYNDGTKYNEKFKGKATLTSDKSSSTAYMELSSL-TSEDSAVYYCGRHFDYYGRG YAVDYWGQGTSVTVSS (SEQ ID NO:22), MDFQVQI-ISFMLISVTVMLSSGEIVLTQSPAL-MAASPGEKVTITCSVSSSISSSYLHWYQQRSETS PKP-WIYGTSNLASGVPVRFSGNGSGTSYSLTISSMEAE-DAATYYCQQWSSYPLTFGGGTKLEIK (SEQ ID NO:38), or MVS-SAQFLGLLLLCFQGTRCDIQMTQTTSSL-SASLGDRVTISCSASQDISNYLNWYQRKPDGTV KLLIYYTSSLHSGVPSRFSGSGSGTDYSLTISNLEPE-DIATYYCLQYSKLPWTFGGGTKLEIK (SEQ ID NO:54). In some embodiments, the antibody or antigen fragment is encoded by a nucleic acid molecule having at least 85% sequence identity to one of the following:

```
                                                      (SEQ ID NO: 4)
  1  atgatggtgt taagtcttct gtacctgttg acagccattc ctggtatcct gtctgatgta 61  cagcttcagg agtcaggacc tggcctcgtg aaaccttctc agtctctgtc tctcacctgc 121  tctgtcactg gctactccat caccagtggt tattactgga actggatccg gcagtttcca
```

-continued

```
181  ggaaacaaac tggaatggat gggctacaca aactacgacg gtagcaataa ctacaaccca 241  tctctcaaaa atcgaatctc catcactcgt gacacatcta agaaccagtt tttcctgaag 301  ttgaattctg tgactactga ggacacaggt acatattact gtgcgggacc ctaccttgac 361  tactggggcc aaggcaccac tctcacagtc tcctca
```

(SEQ ID NO: 20)
```
  1  atggaatgga gcgggatctt tctctttctc ctgtcaggaa ctgcaggtgt ccactttgag 61  gtccagctgc agcagtctgg acctgagctg gtaaagcctg ggcttcagt gaagatgtcc 121  tgcaaggctt ctggatacaa attcactagc aatgttatgc actgggtgaa gcagaagcct 181  gggcagggcc ttgagtggat tggatatatt aatccttaca atgatggtac taagtacaat 241  gagaagttca aggcaaggc cacactgact cagacaaat cctccagcac agcctacatg 301  gagctcagca gcctgacctc tgaggactct gcggtctatt actgtggaag acatttgat 361  tactacggta ggggctacgc tgtggactac tggggtcaag aacctcagt caccgtctcc 421  tca
```

(SEQ ID NO: 36)
```
  1  atggattttc aggtgcagat tatcagcttc atgctaatca gtgtcacagt catgttgtcc 61  agtggagaaa ttgtgctcac acagtctcca gcactcatgg ctgcatctcc aggggagaag 121  gtcaccatca cctgcagtgt cagctcaagt ataagttcca gctacttaca ctggtaccag 181  cagaggtcag aaacctcccc caaaccctgg atttatggca catccaacct ggcttctgga 241  gtccctgttc gcttcagtgg caatggatct gggacctctt attctctcac aataagcagc 301  atggaggctg aagatgctgc cacttattac tgtcaacagt ggagtagtta cccactcacg 361  ttcggagggg ggaccaagct ggaaataaaa
```

(SEQ ID NO: 52)
```
  1  atggtgtcct cagctcagtt ccttggtctc ctgttgctct gttttcaagg taccagatgt 61  gatatccaga tgcacagac tacatcctcc ctgtctgcct ctctgggaga cagagtcacc 121  atcagttgca gtgcaagtca ggacattagc aattatttaa actggtatca acggaaacca 181  gatggaactg ttaaactcct gatctattac acatcaagtt tacactcagg agtcccatca 241  aggttcagtg gcagtgggtc tgggacagat tattctctca ccatcagcaa cctggaacct 301  gaagatattg ccacttacta ttgtctgcag tatagtaagc ttccgtggac gttcggtgga 361  caccaagc tggaaatcaa a.
```

In still other embodiments, the antibody or antigen binding fragment thereof includes amino acid sequences having at least 90% sequence identity to MMVLSLLYLLTAIPG-ILSDVQLQESGPGLVKP-SQSLSLTCSVTGYSITSGYYWNWIRQFPGN-KLEWMGYTNYDGSNNYNPSLKNRISITRDTSKNQ-FFLKLNSVTTEDTGTYYCAGPYLDYWGQGTTL TVSS (SEQ ID NO:6) and MDFQVQIISFM-LISVTVMLSSGEIVLTQSPALMAASPGEKVTITCSVSS-SISSSYLHWYQQRSETSPKPWIYGTSN-LASGVPVRFSGNGSGTSYSLTISSMEAEDAATYY-CQQWSSYPLTFGGGTKLEIK (SEQ ID NO:38).

Another aspect provides an antibody or antigen-binding fragment thereof that specifically binds N$^{w}$-hydroxy-L-Arginine (NOHA) and includes at least three complementarity determining regions (CDRs), wherein the CDRs include polypeptides comprising the amino acid sequences SGYYWN (SEQ ID NO:14), YTNYDGSNNYNPSLKN (SEQ ID NO:16), and PYLDY (SEQ ID NO:18), polypeptides comprising the amino acid sequences SNVMH (SEQ ID NO:30), YINPYNDGTKYNEKFKG (SEQ ID NO:32), and HFDYYGRGYAVDY (SEQ ID NO:34), polypeptides comprising the amino acid sequences SVSSSISSSYLH (SEQ ID NO:46) GTSNLAS (SEQ ID NO:48), and QQWSSYPLT (SEQ ID NO:50), or polypeptides comprising the amino acid sequences SASQDISNYLN (SEQ ID NO:62), YTSSLHS (SEQ ID NO:64), and LQYSKLPWT (SEQ ID NO:66). In some embodiments, the antibody or antigen fragment thereof comprises CDRs having the amino acid sequences SGYYWN (SEQ ID NO:14), YTNYDGSN-NYNPSLKN (SEQ ID NO:16), PYLDY (SEQ ID NO:18), SVSSSISSSYLH (SEQ ID NO:46) GTSNLAS (SEQ ID NO:48), and QQWSSYPLT (SEQ ID NO:50). In some embodiments, the antibody or antigen fragment thereof comprises SGYYWN (SEQ ID NO:14), YTNYDGSN-NYNPSLKN (SEQ ID NO:16), PYLDY (SEQ ID NO:18), SVSSSISSSYLH (SEQ ID NO:46) GTSNLAS (SEQ ID NO:48), and QQWSSYPLT (SEQ ID NO:50). In some embodiments, the antibody or antigen-binding fragment thereof comprises at least one polypeptide having an amino acid sequence having at least 90% sequence identity to MMVLSLLYLLTAIPGILSDVQLQESGPGLVKP-SQSLSLTCSVTGYSITSGYYWNWIRQFPGNKLE WMGYTNYDGSNNYNPSLKNRISITRDTSKNQF-FLKLNSVTTEDTGTYYCAGPYLDYWGQGTTL TVSS (SEQ ID NO:6); MEWSGIFLFLLSGTAGVHFE-VQLQQSGPELVKPGASVKMSCK-ASGYKFTSNVMHWVKQKPGQGLEWIGY-INPYNDGTKYNEKFKGKATLTSDKSSSTAYMELSS-LTSEDSAVYYCGRHFDYYGRG YAVDYWGQGTSVTVSS (SEQ ID NO:22), MDFQVQI-ISFMLISVTVMLSSGEIVLTQSPAL-MAASPGEKVTITCSVSSSISSSYLHWYQQRSETS PKP-WIYGTSNLASGVPVRFSGNGSGTSYSLTISSMEAED-AATYYCQQWSSYPLTFGGGTKLEIK (SEQ ID NO:38), or MVSSAQFLGLLLLCFQGTRCDIQMTQTTSSL-SASLGDRVTISCSASQDISNYLNWYQRKPDGTV KLLIYYTSSLHSGVPSRFSGSGSGTDYSLTISNLEPE-DIATYYCLQYSKLPWTFGGGTKLEIK (SEQ ID NO:54).

In some embodiments, the antibody or antigen binding fragment thereof has an amino acid sequences having at least 90% sequence identity to MMVLSLLYLLTAIPG-ILSDVQLQESGPGLVKP-SQSLSLTCSVTGYSITSGYYWNWIRQFPGNKLE WMGYTNYDGSNNYNPSLKNRISITRDTSKNQF-FLKLNSVTTEDTGTYYCAGPYLDYWGQGTTL TVSS (SEQ ID NO:6) and MDFQVQIISFM-LISVTVMLSSGEIVLTQSPALMAASPGEKVTITCSVSS-SISSSYLHWYQQRSETS PKPWIYGTSN-LASGVPVRFSGNGSGTSYSLTISSMEAEDAATYYC-QQWSSYPLTFGGGTKLEIK (SEQ ID NO:38).

In another aspect, a kit is provided for detecting or monitoring ER− tumors in a subject, the kit comprising an antibody or antigen-binding fragment thereof, that specifically binds N$^w$-hydroxy-L-Arginine (NOHA), or a nucleotide encoding the antibody or antigen-binding fragment thereof.

BRIEF DESCRIPTION OF THE DRAWINGS

The present disclosure is further described in the detailed description which follows, in reference to the noted plurality of drawings by way of non-limiting examples of exemplary embodiments:

FIGS. 2A-2C show measured values for NOHA in culture medium (FIG. 2A), cellular NOS2 expression (FIG. 2B), and cellular nitric oxide (as total nitrite) (FIG. 2C). FIG. 2D is a graph showing the concentration of NOHA in plasma samples. *, represents significance from control/ER+ groups, at $p<0.0$. #, represents significance in ER− ovarian carcinoma versus ER− breast cancer, $p<0.01$; n=6. The legend for the graph in FIG. 2A applies to FIGS. 2B and 2C.

FIG. 5 shows NOHA's stability in dried plasma spots. n=6/group. * significant instability, $p<0.01$.

FIG. 6A is a map of plasmid pSB201-C6 HC 3-6 that comprises a nucleic acid sequence encoding the H1 heavy chain polypeptide. FIG. 6B is a map of plasmid pSB201-C6 HC 1-14 that comprises a nucleic acid sequence encoding the H2 heavy chain polypeptide. FIG. 6C is a map of plasmid pSB201-C6 KC 4-53 that comprises a nucleic acid sequence encoding the L1 light chain polypeptide. FIG. 6D is a map of plasmid pSB201-C6 HC 10-94 that comprises a nucleic acid sequence encoding the L2 light chain polypeptide.

DETAILED DESCRIPTION

Figure 1:
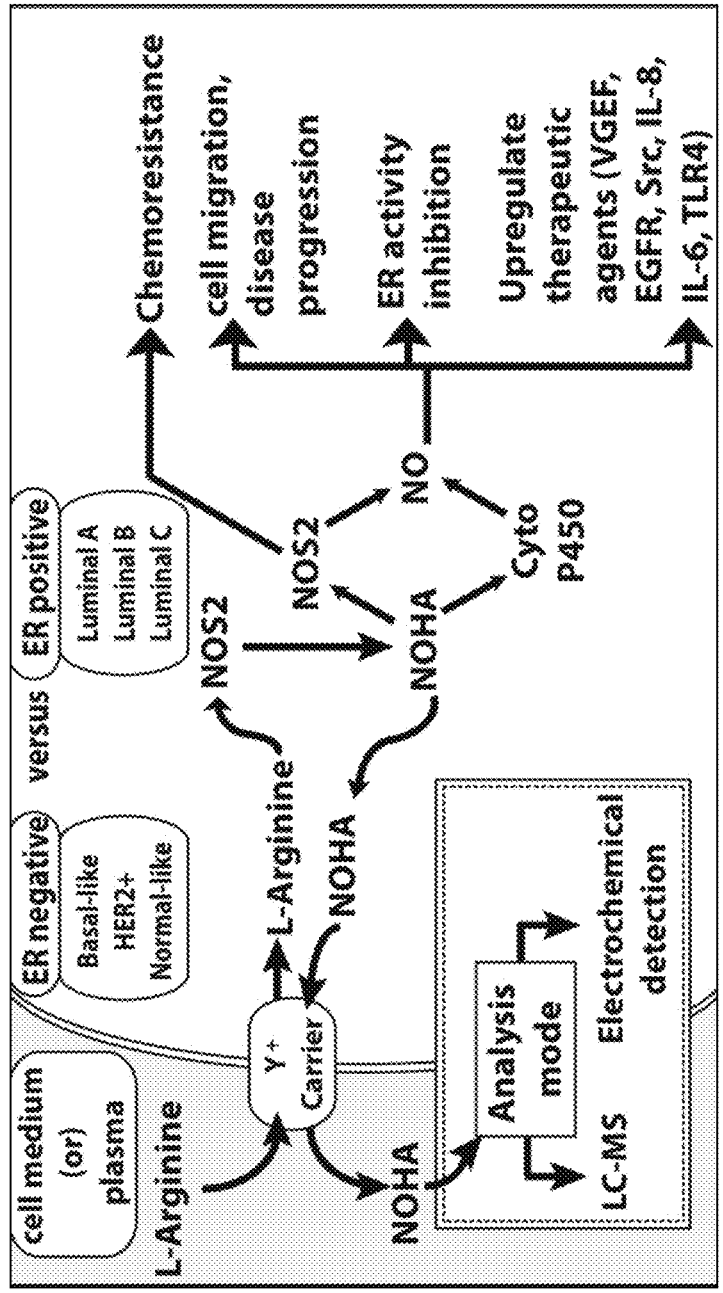
FIG. 1 illustrates the NOHA biochemical pathway.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, the following terms and phrases are intended to have the following meanings:

As used in this specification and the appended claims, the singular forms "a," "an," and "the" include plural references unless the context clearly dictates otherwise. By way of example, "an element" means one element or more than one element. Similarly, references to "the method" includes one or more methods, and/or steps of the type described herein and/or which will become apparent to those persons skilled in the art upon reading this disclosure and so forth.

As used herein, the term "about" means acceptable variations within 20%, within 10%, or within 5% of the stated value.

As used herein the term "Grade 1 tumors" refers to tumors with tumor volume of <250 μm, and comprised of cells that resemble healthy cells (i.e., is well-differentiated or low-grade). A Grade 1 tumor, which is an initial stage of cancer development can, in some embodiments, be targeted drug/gene therapy that focuses on a specific element of a cell, such as a molecule or pathway required for cell growth.

As used herein the term "Grade 2 tumors" refers to tumors at days with tumor volume of ≥400 μm, and comprised of cells that have morphologies less similar to healthy cells (poorly differentiated, intermittent grade of tumor) than those cells in a Grade 1 tumor. In some cases, Grade 2 tumors are associated with onset of an advanced stage of disease. In some embodiments, therapeutic intervention involves a combination of targeted therapy, radiation therapy, chemotherapy, and/or surgery.

As used herein the terms "biomarker" or "marker" generally refer to a protein, nucleic acid molecule, clinical indicator, or other analyte that is associated with a disease. In one embodiment, a marker of breast or ovarian cancer is differentially present in a biological sample obtained from a subject having or at risk of developing breast or ovarian cancer relative to a reference. A marker is differentially present if the mean or median level of the biomarker present in the sample is statistically different from the level present in a control sample. A control sample level may be, for example, the level present in a sample obtained from a healthy control subject or the level obtained from the subject at an earlier timepoint, i.e., prior to treatment. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest. The differential presence of a marker of the invention in a subject sample can be useful in characterizing the subject as having or at risk of developing breast or ovarian cancer, for determining the prognosis of the subject, for evaluating therapeutic efficacy, or for selecting a treatment regimen (e.g., selecting that the subject be evaluated and/or treated by a gynecologic oncology specialist).

As used herein, the acronym "NOHA" refers to $N^w$-hydroxy-L-Arginine (NOHA). All three isoforms of nitric oxide synthase enzyme (viz., NOS1, NOS2, and NOS3) generate NOHA as a stable intermediate during NO production.

An "antibody," as used herein is a protein consisting of one or more polypeptides comprising binding domains substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin structural unit comprises a tetramer that is composed of two identical pairs of polypeptide chains, each pair having one "light" (about 25 kD) and one "heavy" chain (about 50-70 kD). "VL" and "VH" refer to these light and heavy chains respectively.

Antibodies include intact immunoglobulins as well as antigen-binding fragments thereof, which may be produced by digestion with various peptidases, or synthesized de novo either chemically or using recombinant DNA expression technology. Such fragments include, for example, F(ab)2 dimers and Fab monomers. Useful antibodies include single chain antibodies (antibodies that exist as a single polypeptide chain), e.g., single chain Fv antibodies (scFv) in which a VH and a VL chain are joined together (directly or through a peptide linker) to form a continuous polypeptide.

Antibodies also include variants, chimeric antibodies, and humanized antibodies. The term "antibody variant" or "variant" as used herein refers to an antibody with single or multiple mutations in the heavy chains and/or light chains. In some embodiments, the mutations exist in the variable region. In some embodiments, the mutations exist in the constant region. "Chimeric antibodies" refer to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can be conveniently derived from presently known sources using readily available hybridomas or B cells from non-human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the chimeric antibodies are not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

The term "NOHA antibody" as used herein refers to an antibody that immunospecifically binds to NOHA (e.g., its extracellular domain). The antibody may be an isolated antibody. The NOHA antibody binds to NOHA with a dissociation constant (Kd) of 10-6, 10-7, 10-8, 10-9, 10-10, 10-11, 10-12 M or better. For example, the Kd of an antibody-antigen interaction indicates the concentration of antibody (expressed as molarity) at which 50% of antibody and antigen molecules are bound together at thermodynamic equilibrium. Thus, at a suitable fixed antigen concentration, 50% of a higher (i.e., stronger) affinity antibody will bind antigen molecules at a lower antibody concentration than would be required to achieve the same percent binding with a lower affinity antibody. Kd is also the ratio of the kinetic on and off rates (kon and koff); i.e., Kd=koff/kon. A lower Kd value indicates a higher (stronger) affinity.

The term "antigen" refers to a molecule or a portion of a molecule capable of being bound by a selective binding agent, such as an antibody. In some embodiments, an antigen is used to produce antibodies capable of binding to an epitope of that antigen. For example, the antigen can be administered to an animal, which triggers an immune response in the animal that produces antibodies that specifically recognized and bind the antigen. An antigen may have one or more epitopes.

The term "epitope" includes any determinant, for example, a polypeptide determinant, capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, have specific three-dimensional structural characteristics, and/or specific charge characteristics. An epitope is a region of an antigen that is bound by an antibody. In certain embodiments, an antibody specifically binds an antigen when it preferentially recognizes its target antigen in a complex mixture of proteins and/or macromolecules.

"Immunospecific" or "immunospecifically" refers to antibodies that bind, or antibody binding, via domains substantially encoded by immunoglobulin genes or fragments of immunoglobulin genes to one or more epitopes of a protein of interest but do not substantially recognize and bind other molecules in a sample containing a mixed population of antigenic molecules. Typically, an antibody binds immunospecifically to a cognate antigen with a Kd value no greater than 50 nM. In some embodiments, Kd is measured by a surface plasmon resonance assay or a cell binding assay. The use of such assays is well-known in the art.

As used herein, the terms "ER−" and "ER+" refer to estrogen receptor-negative (ER−) and ER-positive (ER+) tumors, two major solid cancer subsets. The ER− subset is the more aggressive subtype and is more difficult to treat than the ER+ subset. Additionally, the ER− subtype is characterized by greater ethnic disparity (two-fold higher in African Americans), worse prognosis, and almost twice the risk of mortality than ER+ tumors. Triple-negative cancers do not express the estrogen receptor, the progesterone receptor or the HER2 receptor (ER−, progesterone-negative and HER2-negative).

The terms "patient" and "subject" include a human or other mammalian animal that receives either prophylactic or therapeutic treatment.

The terms "treat," "treating," and "treatment," as used herein, refer to therapeutic or preventative measures such as those described herein. For example, in some embodiments of the methods of treatment presented herein comprise administering to a patient a treatment regimen in order to prevent, cure, delay, reduce the severity of, or ameliorate one or more symptoms of the disease or disorder or recurring disease or disorder, or in order to prolong the survival of a patient beyond that expected in the absence of such treatment.

The term "effective amount," as used herein, refers to that amount of an agent, which is sufficient to effect treatment, prognosis or diagnosis of ER− cancer, when administered to a patient. A therapeutically effective amount will vary depending upon the patient and disease condition being treated, the weight and age of the patient, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, as provided herein. Dosing may be, e.g., every week, every 2 weeks, every three weeks, every 4 weeks, every 5 weeks, or every 6 weeks. Dosage regimens may be adjusted to provide the optimum therapeutic response. An effective amount is also one in which any toxic or detrimental effects (side effects) of the agent are minimized and/or outweighed by the beneficial effects. In some embodiments, administration is at exactly or about 6 mg/kg or 12 mg/kg weekly, or 12 mg/kg or 24 mg/kg biweekly. Additional dosing regimens are described below. In some embodiments, the administration route is intravenous, intramuscular, epidermal, transdermal, subcutaneous, oral, topical, intraarterial, intrathecal, intraperitoneal, or intraventricular.

Other terms used in the fields of recombinant nucleic acid technology, microbiology, immunology, antibody engineering, and molecular and cell biology as used herein will be generally understood by one of ordinary skill in the applicable arts. For example, conventional techniques may be used for preparing recombinant DNA, performing oligonucleotide synthesis, and practicing tissue culture and transformation (e.g., electroporation, transfection, or lipofection). In some embodiments, enzymatic reactions and purification techniques are performed according to manufacturer's specifications or as commonly accomplished in the art or as described herein. The foregoing techniques and procedures may be generally performed according to conventional methods well known in the art and as described in references that are cited and discussed throughout the present specification. See, e.g., Sambrook et al., 2001, Molecular Cloning: A Laboratory Manual, 3rd ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

By "alteration" or "change" is meant an increase or decrease. An alteration may be by as little as 1%, 2%, 3%, 4%, 5%, 10%, 20%, 30%, or by 40%, 50%, 60%, or even by as much as 70%, 75%, 80%, 90%, or 100%.

By "biologic sample" is meant any tissue, cell, fluid, or other material derived from an organism.

By "capture reagent" is meant a reagent that specifically binds a nucleic acid molecule or polypeptide to select or isolate the nucleic acid molecule or polypeptide.

As used herein, the terms "determining," "assessing," "assaying," "measuring," and "detecting" refer to both quantitative and qualitative determinations, and as such, the term "determining" is used interchangeably herein with "assaying," "measuring," and the like. Where a quantitative determination is intended, the phrase "determining an amount" of an analyte and the like is used. Where a qualitative and/or quantitative determination is intended, the phrase "determining a level" of an analyte or "detecting" an analyte is used.

By "reference" is meant a standard of comparison. For example, in some embodiments, the marker level(s) present in a patient sample is compared to the level of the marker in a corresponding healthy cell or tissue or in a diseased cell or tissue (e.g., a cell or tissue derived from a subject having breast or ovarian cancer). In particular embodiments, the IGFBP2, IL6, FSH, HE4, CA 125; Transthyretin, Transferrin, and/or TAG-72 (CA 72-4) polypeptide level present in a patient sample may be compared to the level of said polypeptide present in a corresponding sample obtained at an earlier time point (i.e., prior to treatment), to a healthy cell or tissue or a neoplastic cell or tissue that lacks a propensity to metastasize. As used herein, the term "sample" includes a biologic sample such as any tissue, cell, fluid, or other material derived from an organism.

By "specifically binds" is meant a compound (e.g., antibody) that recognizes and binds a molecule (e.g., polypeptide) but does not substantially recognize and bind other molecules in a sample, for example, a biological sample.

As used herein the term "comprising," "having," and "including" and the like are used in reference to compositions, methods, and respective component(s) thereof, that are present in a given embodiment, yet open to the inclusion of one more or more unspecified elements. The term "including" is used herein to mean, and is used interchangeably with, the phrase "including but not limited to."

As used herein the term "consisting essentially of" refers to those elements required for a given embodiment. The term permits the presence of additional elements that do not materially affect the basic and novel or functional characteristic(s) of that embodiment of the invention. The term "consisting of" refers to compositions, methods, and respective components thereof as described herein, which are exclusive of any element not recited in that description of the embodiment.

NOHA Biomarkers and Use Thereof

Among the two major solid cancer subsets (including ovarian cancer and breast cancer) of estrogen receptor-negative (ER−) and ER-positive (ER+) tumors, the ER− subset is the more aggressive subtype and is more difficult to treat. The ER− subtype is characterized by greater ethnic disparity (two-fold higher in African American), worse prognosis, and almost twice the risk of mortality than ER+ tumors. ER− cancers can be negative for multiple markers. For example, a triple negative state (e.g., triple negative breast cancer (TNBC)) can be estrogen receptor negative, progesterone receptor negative, and HER2 negative.

Current indicators/markers for ER− and TNBC breast cancer include carcinoembryonic antigen (CEA), which is used to detect colorectal and breast cancer in a blood sample. This marker can be used to screen for advanced stage cancer or tumors and/or cancer recurrence. CA15-3/CA27.29 is used in detection of breast cancer in a blood sample, as well, for advanced metastasis and for cancer or tumor recurrence. No extra-tumoral indicators for early detection are currently known to be used for detecting ER− cancer.

Ovarian cancer is the most lethal gynecological malignancy. Approximately 230,000 women are diagnosed with ovarian cancer each year, and about 150,000 women die from the disease annually. Symptoms for ovarian cancer are generally less evident (if not absent) at early stages and are often more noticeable as the cancer progresses. The standard diagnostic procedure to confirm ovarian cancer is through biopsy of the tissue (usually removed during surgery). Additionally, women with mutations in BRCA1 and/or BRCA2 genes, are not only at risk for an invasive breast cancer development, bur also have about a 50% chance of developing ovarian cancer. The most common type of ovarian cancer, which encompasses nearly 95% of such cases, is ovarian carcinoma. Among the five main subtypes of ovarian carcinoma, high-risk serous carcinoma is the most common and is usually associated with low survival rates. Thus, there is a need for highly reliable biomarker for early detection and progression monitoring for ovarian cancer.

ER+ serous ovarian carcinoma patients have a better overall and progression-free survival than ER− patients. While the estrogen-hormone receptor expression subtypes (i.e., ER+ and ER−) have a well-established prognostic and treatment-predictive role in breast cancer, their roles in ovarian cancer are less well-defined. Thus, identification of similar prognostic and predictive factors based on estrogen-hormone receptor expression status would be useful to better navigate diagnosis, treatment, and therapy management in ovarian cancer patients.

Both ovarian cancer and breast cancer have been shown to express markers of inflammation. While inflammation is usually considered to be a major component of the tumor microenvironment and to play a causative role in cancer initiation, promotion, and progression; several pro-inflammatory proteins (viz., COX2, NF-kB, IL-6, IL-8, S100 calcium binding protein, and VEGF) that directly correlate with the upregulation of the inflammation-associated enzyme (viz., inducible nitric oxide synthase, NOS2), have shown inconsistent results as tumor biomarker. In contrast, NOS2 has been recently identified as a key feed-forward signaling regulator in promoting chronic inflammation and breast or ovarian cancer progression. High NOS2 expression has been associated with decreased survival among ER− breast or ovarian cancer patients, in contrast to ER+ patients.

Of added interest, multiple clinical studies involving serous and other ovarian carcinoma patients suggest that NOS2 upregulation is a potential prognostic marker for ovarian cancer. However, the correlation between NOS2 feed-forward regulation and estrogen hormone receptor expression status that were well-defined in breast-cancer, remains unclear for ovarian carcinomas (e.g., serous ovarian carcinoma).

Nw-hydroxy-L-Arginine (NOHA) is a molecule detectable in a blood sample that can be used to distinguish between ER− and ER+ breast or ovarian cancer. In some embodiments, the presence of NOHA in a blood sample can be used to differentiate between ER− high grade and low-grade tumors. NOHA also correlates with the ER− molecular phenotype with 100% sensitivity and specificity (at 95% confidence interval of 94.5% to 100% for both). Accordingly, in some embodiments, NOHA can be used to diagnose ER− and ER+ serous ovarian carcinoma.

Inflammation is a major component of the tumor microenvironment and a driving force in cancer initiation, promotion, and progression. The inflammation-associated enzyme, inducible nitric oxide synthase (NOS2), has recently emerged as a candidate oncogene in ER− breast or ovarian cancer. Upregulation in NOS2 expression has been associated with disease aggressiveness and poor survival. Although observations implicate NOS2 as an attractive therapeutic target, the roles of NOS2 upregulation in ER− cancer progression among ethnically diverse groups is currently unclear; and current markers that could directly correlate with NOS2 (viz., epidermal growth factor receptor; vascular endothelial growth factor; and poly-adenosine-diphosphate ribose polymerase inhibitors) show inconsistent results in ethnically distinctive populations.

NOS2 feed forward regulation is a primary indicator of inflammation, is upstream to current breast or ovarian cancer markers (VEGF, Src, EGFR, etc.), and shows aberrant expression in many solid tumors including breast cancer, colon cancer, and melanoma. The drawback is that NOS2 is not extra-tumoral and ethnic specificities, or lack thereof, are unknown.

All three isoforms of nitric oxide synthase enzyme (viz., NOS1, NOS2 and NOS3) generates Nw-hydroxy-L-Arginine (NOHA) as a stable intermediate during NO production. Only cells expressing the calcium independent NOS2 (viz., EMT-6 mammary adenocarcinoma cells, RAW 264.7 macrophages) have been shown to liberate substantial amounts of NOHA to accumulate in culture medium or in circulating blood. No other sources other than the three nitric oxide synthase isozymes appear to generate NOHA.

As seen in FIG. 1, NOHA is a stable intermediate of L-arginine utilization by NOS. While all three NOS isozymes (NOS1, NOS2, and NOS3) produce NOHA, only Ca2+ independent NOS2 can liberate NOHA into the extracellular matrix. Liberated NOHA competes with L-arginine for the same amino acid carrier (y+ system) for its cellular re-absorption. Because NOS exhibits a two-fold higher Km requirement for NOHA than L-arginine, cellular re-uptake of NOHA and its metabolism will only be possible when the extracellular and intracellular L-arginine concentrations fall drastically below a critical threshold limit.

According to some aspects of the present disclosure, NOHA can be used as a sensitive and reliable biomarker for ER− ovarian cancer or breast cancer early prognosis. In some embodiments, the methods of the present disclosure test for extracellular or circulating NOHA.

In some embodiments, a reduction in the NOHA levels in a sample compared to NOHA levels observed in a control sample (e.g., a sample derived from a healthy subject) indicates a presence of ER-ovarian cancer or breast cancer. In some embodiments, the NOHA reduction is statistically significant (for example, p-value of less than 0.01). In some embodiments, the change in the NOHA level may simply be a general trend of reduction in the NOHA level.

In some embodiments, such prognosis may be made based on ethnic orientation, that is, NOHA has been shown to exhibit ethnic specificity in patients. In some embodiments, a greater reduction in the NOHA levels can be observed in African American patients than in Caucasian patients.

Understanding the ethnic specificity of NOHA in ER− breast or ovarian cancer is desirable as there is greater ethnic disparity among ER− breast tumor with 2 to 3-fold higher instances among African American populations, with earlier onset than other ethnic origins. In addition to showing ethnic disparity in NOHA reduction between ER− in Caucasians (CA) and ER− in African Americans (AA), when Jewish, Asian, and Hispanic samples were accessed to determine NOHA reduction based on ER expression, a significant reduction in NOHA was identified for ER− Jewish, Asian and Hispanic populations compared to healthy or ER+ groups. The reduction of NOHA levels observed in ER− Jewish subjects was ≥24% more than those of ER− Asian or ER− Hispanic subjects. However, the greatest NOHA reduction was observed in the ER− AA population. The reduction of NOHA levels in ER− Asian, ER− Hispanic, and ER− CA groups were comparable to one another. Plasma NOHA for ER+ and healthy groups were comparable to one another with no ethnic-specific difference. In some embodiments, the clinical relevance of NOHA as a selective prognostic marker for ER− breast or ovarian cancer patients, with favorable ethnic selectivity, is utilized to make the present methods of detection and monitoring ER− breast or ovarian cancer more precise.

In some embodiments, the close correlation of NOHA reduction based on ethnicity is used to detect a heterogeneous disease such as cancer. In some embodiments, NOHA detection is used as a predictive indicator of whether an individual will develop aggressive cancer. In some embodiments, detection of NOHA precedes cyst or tumor development. Based on ethnicity, the aggressive cancer subtypes such as ER− and triple negative breast or ovarian cancer can occur more frequently in much younger individuals (such as in African Americans, where such aggressive breast or ovarian cancer can occur in individuals in their mid-20's), which can be before their scheduled screening, which generally would be administered when the subject was in his/her 40's). In some embodiments, NOHA levels are used to screen for the presence of such cancers. In some embodiments, since aberrant changes with the enzyme responsible for NOHA production are seen with other solid tumors (viz., lung, colon, prostate and melanoma), the predictive response of NOHA (seen here with breast or ovarian cancer; as an immediate outcome) is used with other solid tumors (viz., as extended outcome), in similar fashion as outlined above.

In some embodiments, monitoring the NOHA levels can be used to determine a severity of tumor. For example, in some embodiments, a reduction in the NOHA levels indicates a change in tumor severity from Grade 1 tumor to Grade 2 tumor, and an increase in the levels of NOHA may indicate an improvement in a subject's condition. In some embodiments, levels of extra-cellular NOHA are detected and monitored. Tumor grades can usually be determined by the Nottingham grading system (viz., low-grade or grade 1, in which cancer cells resemble normal cells and are not growing rapidly; intermediate-grade or grade 2, in which cells do not resemble normal cells and are growing faster than in low or grade 1; and, high/advanced-grade or grade 3, in which cancer cells have an abnormal morphology and may grow or spread more aggressively). In some embodiments, NOHA levels are measured for prognosis on disease aggressiveness. In some embodiments, NOHA levels are used for planning tumor prognosis and disease treatment, and to avoid the metastasis ambiguity (that is associated while staging such aggressive tumor). In some embodiments, the methods of the present disclosure include monitoring the progressive change (increase or decrease) in NOHA levels to determine tumor volume or grade.

For example, a 0.85-fold reduction in the amount of NOHA in a sample derived from a Caucasian subject with an ER− tumor * or a 1.9-fold reduction in a sample derived from an African American with an ER− tumor is characteristic of Grade 1 tumors. Grade 1 tumor cells resemble normal cells and do not growing rapidly. A 3.9-fold reduction in the amount of NOHA in a sample derived from a Caucasian subject with an ER− tumor or a 9.4-fold reduction in a sample derived from an African America subject ER− AA is characteristic of Grade 3/advance tumors, in which cancer cells have abnormal morphologies and can grow or spread more aggressively. An intermediate NOHA level, i.e., a level between those levels characteristic of Grade 1 and 3 tumors, would be representative of a Grade 2 tumor, in which cells do not resemble normal cells and are growing faster, but have not started to spread.

In one aspect, the present disclosure provides a method of detecting a level of NOHA in a subject, the method comprising obtaining a sample from a subject and detecting an amount of NOHA in the sample. In some embodiments, the amount of NOHA in the subject's sample is compared to an amount of NOHA in a control sample, which can be derived from a healthy subject or can be a previously-obtained sample from the same subject. In some embodiments, the amount of NOHA in the subject's sample is compared to a reference value. The amount of NOHA can be detected by a variety of methods known in the art, as described in more detail below. For example, in some embodiments, the amount of NOHA can be detected by contacting the sample with an antibody that specifically binds NOHA and detecting binding between NOHA and the antibody, but other methods can also be used.

In another aspect, the present disclosure provides a method for detecting ER− breast or ovarian cancer in a subject, the method comprising obtaining a sample from a subject suffering from breast or ovarian cancer, determining an amount of NOHA in the subject sample; and comparing the amount of NOHA in the subject sample to the amount of NOHA in a control sample, wherein a lesser amount of NOHA in the subject sample indicates presence of ER− breast or ovarian cancer in the subject.

In some aspects, methods for determining the course of ER− ovarian cancer or breast cancer in a subject are provided. Disease course refers to changes in disease status over time, including disease progression (worsening) and disease regression (improvement). Over time, the amounts or relative amounts (e.g., the pattern) of biomarkers change. Accordingly, in some embodiments, the present methods include measuring the amount of NOHA in a subject at two or more different time points, e.g., a first time and a second time, and comparing the amounts determined at the different time points, if any. The course of disease (e.g., during treatment) is determined based on these comparisons.

In an aspect, the present disclosure provides a method for monitoring a treatment regimen for ER− ovarian cancer or breast cancer, the method comprising determining an amount of NOHA in a first sample obtained or derived from a subject suffering from ER− ovarian cancer or breast cancer prior to administering a treatment regimen; determining an amount of NOHA in a second sample taken from the subject subsequent to commencement of the treatment regimen; and comparing the amounts of NOHA in the first sample and the second sample, wherein a greater amount of NOHA in the second sample indicates the subject's responsiveness to the treatment regimen. For example, an increase of at least a half-fold in the amount of NOHA after a specific therapeutic treatment (viz., chemotherapy) is indicative of a positive effect attributable to the treatment, while no change in NOHA amounts (or a decrease) in comparison to NOHA amounts prior to such treatment would be representative of an ineffective treatment (or a negative treatment outcome).

In another embodiment, the present disclosure provides a method of identifying therapeutic agents that target ER− ovarian cancer or breast cancer, the method comprising determining a level of NOHA in a first sample taken from a subject suffering from ER− ovarian cancer or breast cancer prior to administering a therapeutic agent; determining an amount of NOHA in a second sample obtained or derived from the subject subsequent to administering the therapeutic agent; and comparing the amount of NOHA in the first sample and the second sample, wherein a greater amount of NOHA in the second sample indicates that the agent is effective in targeting ER− breast or ovarian cancer in the subject.

In an aspect, a method is provided for prognosis of a tumor comprises monitoring NOHA that is liberated from cells expressing NOS2. In some embodiments, monitoring comprises generating a specific index for tumor prognosis. In some embodiments, the index includes expected amounts of NOHA in a healthy individual or an individual having a tumor of a specific grade. In some embodiments, the data in the index includes values averaged for all ethnicities or different values for individuals of different ethnicities. For example, when compared to healthy individual NOHA level, a reduction by at least half-fold can be indicative of an individual, irrespective of their ethnicity, that is more likely to develop aggressive ovarian cancer or breast cancer (e.g., ER− ovarian cancer or breast cancer).

In some embodiments, monitoring NOHA amounts further comprises generating a specific and more reliable index for tumor prognosis in racially diverse groups. In some embodiments, the racially diverse groups are African American and Caucasians populations, wherein each racially diverse group has different indexes for tumor prognosis. In some embodiments, the racially diverse groups are Asians, Hispanics or Mongolians. In some embodiments, the index includes the amounts of NOHA expected in individuals having different ethnic backgrounds. In some embodiments, the index includes a correlation between a change in the amounts of NOHA and status of cancer or prognosis of cancer for specific ethnic groups. Based on ethnicity, a 1-fold decrease in NOHA compared those of healthy individuals would suggest ER− ovarian cancer or breast cancer onset in those individuals of Caucasian origin. These subjects would be considered to have developed a low-grade tumor and are at an early stage of the disease. Such a Caucasian patient would, in some embodiments, undergo additional diagnostic screening (viz., morphological imaging such as immunohistochemistry analysis, genetic screening for additional biomarkers related with such aggressive cancer, etc.), and in some embodiments, the additional screening would be followed with consultation for a treatment regimen. However, an African American patient with only a 1-fold NOHA reduction would be more likely (or has the potential) to develop an aggressive tumor like ER− breast or ovarian cancer in the near future and would be advised to self-monitor (using a NOHA home-kit assay, daily for 2 weeks), or be screened at a diagnostic center twice a week (for 2 weeks). In some embodiments, such diagnostic measures would be accompanied or preceded by genetic counseling to better understand the potential risk of developing such aggressive tumor. Thus, analysis of the extent of NOHA reduction based on ethnicity allows for personalizing cancer care and provides better monitoring of treatment outcome.

In some embodiments, monitoring extracellular and intracellular concentration of L-arginine below a critical threshold is a proxy for monitoring NOHA. High NOS2 expression and nitric oxide production are indicators for poor ER– ovarian cancer or breast cancer survival. L-arginine, is the substrate for NOS2 mediated NOHA and nitric oxide production. High NOS2 expression favors increased L-arginine uptake (for cellular nitric oxide production). This results in higher intracellular L-Arginine concentration, and a reduction in the extracellular L-Arginine and NOHA levels.

In some embodiments, monitoring the amount of NOHA further comprises defining a predictive response between ER– tumor ethnic groups. In some embodiments, the predictive response comprises a better therapy outcome measurement. In some embodiments, the predictive response comprises preventing unnecessary exposure of unresponsive patients to ineffective therapy.

In some embodiments, monitoring NOHA allows for predicting ethnic-specific responses in other solid tumor or cancer prognosis. In some embodiments, the tumor is a breast tumor. In some embodiments, the tumor is an ovarian, brain, prostrate, lung, liver, pancreatic, colon, rectal, and kidney/renal. In some embodiments, the cancer is a melanoma, sarcoma or a lymphoma.

In some embodiments, monitoring the amount of NOHA further comprises a method for measuring therapy outcome, wherein NOHA levels are measured to determine if a particular therapy is beneficial or not and thus inform individualizing of therapy. In some embodiments, the monitoring further comprises determining a chemo-resistance pattern for the patient. In some embodiments, the monitoring further comprises determining tumor migration and tumor response under environmental stimuli.

Detection of NOHA

The level of NOHA biomarker can be detected in a biological sample of the subject (e.g., tissue or biological fluid). Suitable samples, include, but are not limited to, blood, blood serum, plasma, saliva, urine, ascites, cyst fluid, a homogenized tissue sample (e.g., a tissue sample obtained by biopsy), a cell isolated from a patient sample, and similar samples of tissue or bodily fluid.

NOHA can be detected by any suitable method. The methods described herein can be used individually or in combination for a more accurate detection of the biomarkers (e.g., biochip in combination with mass spectrometry, immunoassay in combination with mass spectrometry, and the like).

Methods for detecting NOHA include, but are not limited to, optical methods, electrochemical methods (voltametry and amperometry techniques), atomic force microscopy, and radio frequency methods (e.g., multipolar resonance spectroscopy).

In some embodiments, the levels of NOHA can be measured by immunoassay. Immunoassays typically utilize an antibody (or other agent that specifically binds the marker) to detect the presence or absence of a biomarker (e.g., NOHA) in a sample. In some methods, the amount of NOHA present in a sample can be quantified using methods known in the art. Antibodies can be produced by methods well-known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. As used herein, the term "antibody" means not only intact antibody molecules, but also fragments of antibody molecules that retain immunogen-binding ability. Such fragments are also well known in the art and are regularly employed both in vitro and in vivo. Examples of antibody fragments include, but are not limited to, Fab, Fab', F(ab')2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments.

The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426). For example, F(ab')2, and Fab fragments that lack the Fc fragment of an intact antibody, clear more rapidly from the circulation, and may have less non-specific tissue binding than an intact antibody (Wahl et al., J. Nucl. Med. 24:316 325 (1983). Thus, the antibodies of the invention comprise, without limitation, whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake. See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and using unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including VH- and VL-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In various embodiments, an antibody is monoclonal. Alternatively, the antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')2" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Methods of preparing antibodies are well known to those of ordinary skill in the science of immunology. Antibodies can be made by any of the methods known in the art utilizing a soluble polypeptide, or immunogenic fragment thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding polypeptides or immunogenic fragments thereof, can be provided to the host in a delivery vehicle that is taken up by immune cells of the host. The cells will in turn express the polypeptide thereby generating an immunogenic response in the host. Alternatively, nucleic acid sequences encoding human polypeptides or immunogenic fragments thereof, can be expressed in cells in vitro, followed by isolation of the polypeptide and administration of the polypeptide to a suitable host in which antibodies are raised.

Alternatively, antibodies may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well-known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Suitable immunoassay detection methods include, for example, Western blot, sandwich immunoassays including ELISA and other enzyme immunoassays, fluorescence-based immunoassays, and chemiluminescence. Nephelometry is an assay done in liquid phase, in which antibodies are in solution. Binding of the antigen to the antibody results in changes in absorbance, which is measured. Other forms of immunoassay include magnetic immunoassay, radioimmunoassay, and real-time immunoquantitative PCR (iqPCR).

In some embodiments, the level of NOHA can be detected by mass spectrometry (MS). Mass spectrometry is a well-known tool for analyzing chemical compounds that employs a mass spectrometer to detect gas phase ions. Mass spectrometers are well known in the art and include, but are not limited to, time-of-flight, magnetic sector, quadrupole filter, ion trap, ion cyclotron resonance, electrostatic sector analyzer and hybrids of these. In some embodiments, the method is performed in an automated (Villanueva et al., Nature Protocols (2006) 1(2):880-891) or semi-automated format. This can be accomplished, for example with the mass spectrometer operably linked to a liquid chromatography device (LC-MS/MS or LC-MS) or gas chromatography device (GC-MS or GC-MS/MS).

In some embodiments, NOHA levels are monitored by ELISA. In some embodiments, NOHA levels can be determined by an LC-MS method or via an electrochemical detection method using micro-electrodes (either static-cell or flow-cell electrodes). In some embodiments, the monitoring may comprise colorimetric, chemiluminescence or fluorometric assays. However, as noted above, other known methods or techniques can be used to detect the level of NOHA.

In some aspects, the present disclosure provides NOHA antibodies that can be used for ELISA assays. Various methods can be used to prepare such NOHA antibodies. The steps for making custom antibodies for ELISA assays include conjugating a carrier protein and small molecule where a small molecule (such as NOHA) is not sufficiently complex by itself to induce an immune response or be processed in a manner that elicits production of specific antibodies. For antibody production to be successful with small antigens, they must be chemically conjugated with immunogenic carrier proteins (such as keyhole limpet hemocyanin (KLH)). Adjuvants can be mixed and injected with an immunogen to increase the intensity of the immune response. The method also includes a step of immunization. For example, several (e.g., 5) mice (balb/c) can be immunized with NOHA-positive serum. Those animals that are the best producers of antibodies can be taken to the next stage of fusion. ELISA evaluation of titer can be performed prior to selection for hybridoma fusion. In some embodiments, approximately 3-4 mg of protein immunogen (or) 3 mg of conjugated peptide and 0.5 mg of free peptide are required for this stage. The method, in some embodiments, also includes fusion step. For example, once an acceptable titer is obtained, hybridoma fusion can be performed using splenocytes from mouse with the best titer and myeloma cells. Supernatant from the growing hybridoma wells can be screened by ELISA. Next, desirable parental clones, once identified, are subjected to sub-cloning. For example, desirable parental clone can be sub-cloned by limiting dilution. The selected cells can be sub-cultured in vitro and isotyped. Hybridoma cells can be cryopreserved.

In some embodiments, a NOHA antibody comprises a sequence that has at least about 50% identity, at least about 60%, at least about 70%, at least about 80%, at least about 90%, at least about 95%, at least about 98% identity or at least about 99% identity to sequences discussed in this disclosure.

In some embodiments, a NOHA antibody comprises a sequence: ADAAPTVSIFPPSSEQLTSG-GASVVCFLNNFYPKDINVKWKIDGSERQNGVLN-SWTDQDSKDST YSMSSTLTLTKDEYERHNSYT-CEATHKTSTSPIVKASFNRNEC (SEQ ID NO:1). One of ordinary skill in the art would be able to ascertain the CDRs by analyzing SEQ ID NO:1, e.g., based on the Kabat or Chothia definition. Thus, antibodies, or antigen-binding fragments thereof, having the CDRs of SEQ ID NO:1, e.g., CDR-L1, CDR-L2, CDR-L3, CDR-H1, CDR-H2 and CDR-H3, are also part of the present disclosure. The antibody having the amino acid sequence of SEQ ID NO:1 has been shown to be effective in detecting breast cancer (see U.S. Pat. No. 10,073,099, the contents of which are hereby incorporated by reference in their entirety).

In some embodiments, a NOHA antibody comprises a sequence that has at least about 50% identity, at least about 60%, at least about 70%, at least about 80%, at least about 90%, at least about 95%, at least about 98% identity or at least about 99% identity to SEQ ID NO:1. In some embodiments, a NOHA antibody comprises a sequence that has at least about 50% identity, at least about 60%, at least about 70%, at least about 80%, at least about 90%, at least about 95%, at least about 98% identity or at least about 99% identity to SEQ ID NO:1 and comprises KTSTS (SEQ ID NO:2) at amino acid residues 91-95 of SEQ ID NO:1. In some embodiments, a NOHA antibody comprises KTSTS (SEQ ID NO:2) at amino acid residues 91-95 of SEQ ID NO:1. In some embodiments, a NOHA antibody has a sequence comprising amino acid residues 85-95 of SEQ ID NO:1. In some embodiments, a NOHA antibody has a sequence comprising amino acid residues 80-95 of SEQ ID NO:1. In some embodiments, a NOHA antibody has a sequence comprising amino acid residues 75-95 of SEQ ID NO:1. In some embodiments, a NOHA antibody has a sequence comprising amino acid residues 70-95 of SEQ ID NO:1. In some embodiments, a NOHA antibody has a sequence comprising amino acid residues 65-95 of SEQ ID NO:1.

In some embodiments, a NOHA antibody has a sequence comprising amino acid residues 91-100 of SEQ ID NO:1. In some embodiments, a NOHA antibody has a sequence comprising amino acid residues 90-100 of SEQ ID NO:1. In some embodiments, a NOHA antibody has a sequence comprising amino acid residues 85-100 of SEQ ID NO:1. In some embodiments, a NOHA antibody has a sequence comprising amino acid residues 80-100 of SEQ ID NO:1. In some embodiments, a NOHA antibody has a sequence comprising amino acid residues 75-100 of SEQ ID NO:1. In some embodiments, a NOHA antibody has a sequence comprising amino acid residues 70-100 of SEQ ID NO:1. In some embodiments, a NOHA antibody has a sequence comprising amino acid residues 65-100 of SEQ ID NO:1.

In some embodiments, a NOHA antibody has a sequence comprising amino acid residues 91-105 of SEQ ID NO:1. In some embodiments, a NOHA antibody has a sequence comprising amino acid residues 90-105 of SEQ ID NO:1. In some embodiments, a NOHA antibody has a sequence comprising amino acid residues 85-105 of SEQ ID NO:1. In some embodiments, a NOHA antibody has a sequence comprising amino acid residues 80-105 of SEQ ID NO:1. In some embodiments, a NOHA antibody has a sequence comprising amino acid residues 75-105 of SEQ ID NO:1. In some embodiments, a NOHA antibody has a sequence comprising amino acid residues 70-105 of SEQ ID NO:1. In some embodiments, a NOHA antibody has a sequence comprising amino acid residues 65-105 of SEQ ID NO:1.

In some embodiments, the NOHA monoclonal antibody sequence includes one or more combinations of heavy chain sequences (LOCUS C6_VH3-6_G1 (H1 or LOCUS H1) and LOCUS C6_VH1-14_G2a (H2 or LOCUS H2)) and light chain sequences (LOCUS C6_VK4-53 (L1 or LOCUS L1) and LOCUS C6_VK10-94 (L2 or LOCUS L2)).

The nucleic acid sequence for H1 is below:

SEQ ID NO: 4

```
  1  atgatggtgt taagtcttct gtacctgttg acagccattc ctggtatcct gtctgatgta 61  cagcttcagg agtcaggacc tggcctcgtg aaaccttctc agtctctgtc tctcacctgc 121  tctgtcactg gctactccat caccagtggt tattactgga actggatccg gcagtttcca 181  ggaaacaaac tggaatggat gggctacaca aactacgacg gtagcaataa ctacaaccca 241  tctctcaaaa atcgaatctc catcactcgt gacacatcta agaaccagtt tttcctgaag 301  ttgaattctg tgactactga ggacacaggt acatattact gtgcgggacc ctaccttgac 361  tactggggcc aaggcaccac tctcacagtc tcctca
```

The amino acid sequence for H1 is below:

(SEQ ID NO: 6)
MMVLSLLYLLTAIPGILSDVQLQESGPGLVKPSQSLSLTCSVTGYSITSGY
YWNWIRQFPGNKLEWMGYTNYDGSNNYNPSLKNRISITRDTSKNQFFLKLN
SVTTEDTGTYYCAGPYLDYWGQGTTLTVSS

The CDR sequences for H1 are in the Table 1 below:

TABLE A

| Heavy Chain: H1 | Nucleic Acid Sequence) | Nucleotide Position | Amino acid sequence |
|---|---|---|---|
| CDR1 | agtggt tattactgga ac (SEQ ID NO: 8) | 145-162 | SGYWN (SEQ ID NO: 14) |
| CDR2 | tacaca aactacgacg gtagcaataa ctacaa cccatctctcaaaa at (SEQ ID NO: 10) | 205-252 | YTNYDGSNNYNPSLKN (SEQ ID NO: 16) |
| CDR3 | cc taccttgac tac (SEQ ID NO: 12) | 349-363 | PYLDY (SEQ ID NO: 18) |

The nucleic acid sequence for H2 is below:

(SEQ ID NO: 20)
```
  1 atggaatgga gcgggatctt tctctttctc ctgtcaggaa ctgcaggtgt ccactttgag
 61 gtccagctgc agcagtctgg acctgagctg gtaaagcctg gggcttcagt gaagatgtcc
121 tgcaaggctt ctggatacaa attcactagc aatgttatgc actgggtgaa gcagaagcct
181 gggcagggcc ttgagtggat tggatatatt aatccttaca atgatggtac taagtacaat
241 gagaagttca aaggcaaggc cacactgact tcagacaaat cctccagcac agcctacatg
301 gagctcagca gcctgacctc tgaggactct gcggtctatt actgtggaag acattttgat
361 tactacggta ggggctacgc tgtggactac tggggtcaag aacctcagt caccgtctcc
421 tca
```

The amino acid sequences for H2 is below:

(SEQ ID NO: 22)
MEWSGIFLFLLSGTAGVHFEVQLQQSGPELVKPGASVKMSCKASGYKFTSN
VMHWVKQKPGQGLEWIGYINPYNDGTKYNEKFKGKATLTSDKSSSTAYMEL
SSLTSEDSAVYYCGRHFDYYGRGYAVDYWGQGTSVTVSS

The CDR sequences for H2 are in the Table 2 below:

TABLE B

| Heavy Chain: H2 | Nucleic Acid Sequence) | Nucleotide Position | Amino acid sequence |
|---|---|---|---|
| CDR1 | agc aatgttatgc ac (SEQ ID NO: 24) | 148-162 | SNVMH (SEQ ID NO: 30) |
| CDR2 | tatatt aatccttaca atgatggtac taagtac aatgagaagttca aagg c (SEQ ID NO: 26) | 205-255 | YINPYNDGTKYN EKFKG (SEQ ID NO: 32) |
| CDR3 | cattttgat tactacgg taggggctacgc tgtgg actac(SEQ ID NO: 28) | 352-390 | HFDYYGRGYAVDY (SEQ ID NO: 34) |

The nucleic acid sequence for L1 is below:

```
                                                        (SEQ ID NO: 36)
  1   atggattttc aggtgcagat tatcagcttc atgctaatca gtgtcacagt catgttgtcc 61   agtggagaaa ttgtgctcac acagtctcca gcactcatgg ctgcatctcc aggggagaag 121   gtcaccatca cctgcagtgt cagctcaagt ataagttcca gctacttaca ctggtaccag 181   cagaggtcag aaacctcccc caaaccctgg atttatggca catccaacct ggcttctgga 241   gtccctgttc gcttcagtgg caatggatct gggacctctt attctctcac aataagcagc 301   atggaggctg aagatgctgc cacttattac tgtcaacagt ggagtagtta cccactcacg 361   ttcggagggg ggaccaagct ggaaataaaa
```

The amino acid sequence for L1 is below:

(SEQ ID NO: 38)
MDFQVQIISFMLISVTVMLSSGEIVLTQSPALMAASPGEKVTITCSVSSSI

SSSYLHWYQQRSETSPKPWIYGTSNLASGVPVRFSGNGSGTSYSLTISSME

AEDAATYYCQQWSSYPLTFGGGTKLEIK

The CDR sequences for L1 are in the Table 3 below:

TABLE C

| Light Chain: L1 | Nucleic Acid Sequence) | Nucleotide Position | Amino acid sequence |
|---|---|---|---|
| CDR1 | agtgt cagctcaagt ataagttcca gctacttaca c (SEQ ID NO: 40) | 136-171 | SVSSSISSSYLH (SEQ ID NO: 46) |
| CDR2 | ggca catccaacct ggcttct (SEQ ID NO: 42) | 217-237 | GTSNLAS (SEQ ID NO: 48) |
| CDR3 | caacagt ggagtagtta cccactcacg (SEQ ID NO: 44) | 334-360 | QQWSSYPLT (SEQ ID NO: 50) |

The nucleic acid sequence for L2 is below:

```
                                                        (SEQ ID NO: 52)
  1   atggtgtcct cagctcagtt ccttggtctc ctgttgctct gttttcaagg taccagatgt 61   gatatccaga tgacacagac tacatcctcc ctgtctgcct ctctgggaga cagagtcacc 121   atcagttgca gtgcaagtca ggacattagc aattatttaa actggtatca acggaaacca 181   gatggaactg ttaaactcct gatctattac acatcaagtt tacactcagg agtcccatca 241   aggttcagtg gcagtgggtc tgggacagat tattctctca ccatcagcaa cctggaacct 301   gaagatattg ccacttacta ttgtctgcag tatagtaagc ttccgtggac gttcggtgga 361   ggcaccaagc tggaaatcaa a
```

The amino acid sequence for L2 is below:

(SEQ ID NO: 54)
MVSSAQFLGLLLLCFQGTRCDIQMTQTTSSLSASLGDRVTISCSASQDISN

YLNWYQRKPDGTVKLLIYYTSSLHSGVPSRFSGSGSGTDYSLTISNLEPED

IATYYCLQYSKLPWTFGGGTKLEIK

The CDR sequences for L2 are in the Table 4 below:

TABLE D

| Light Chain: L2 | Nucleic Acid Sequence) | Nucleotide Position | Amino acid sequence |
|---|---|---|---|
| CDR1 | a gtgcaagtca ggacattagc aattatttaa ac (SEQ ID NO: 56) | 130-162 | SASQDISNYLN (SEQ ID NO: 62) |
| CDR2 | tac acatcaagtt tacactca (SEQ ID NO: 58) | 208-228 | YTSSLHS (SEQ ID NO: 64) |
| CDR3 | ctgcag tatagtaagc ttccgtggac g (SEQ ID NO:60 | 325-351 | LQYSKLPWT (SEQ ID NO: 66) |

In some embodiments, the NOHA antibody includes two heavy chain sequences and two light chain sequences. In some embodiments, the NOHA antibody may comprises a combination of at least one of the above-mentioned heavy chain sequences with at least one of the above-mentioned light chain sequences.

In some embodiments, an antibody, or antigen binding fragment thereof, comprises an amino acid sequence having at least 90% sequence identity to MMVLSLLYLLTAIPG-ILSDVQLQESGPGLVKP-SQSLSLTCSVTGYSITSGYYWNWIRQFPGNKLE WMGYTNYDGSNNYNPSLKNRISITRDTSKNQF-FLKLNSVTTEDTGTYYCAGPYLDYWGQGTTL TVSS (SEQ NO:6). In some embodiments, an antibody or antigen binding fragment thereof comprises a complementarity determining region (CDR) having the amino acid sequence SGYYWN (SEQ ID NO:14). In some embodiments an antibody, or antigen binding fragment thereof comprises a CDR having the amino acid sequence YTNYDGSNNYNPSLKN (SEQ ID NO:16). In some embodiments, an antibody, or antigen binding fragment thereof, comprises a CDR having the amino acid sequence PYLDY (SEQ ID NO:18).

In some embodiments of the present disclosure, an antibody, or antigen binding fragment thereof, comprises an amino acid sequence having at least 90% sequence identity to MEWSGIFLFLLSGTAGVHFEVQLQQSGPELVKPGASVKMSCKASGYKFTSNVMHWVKQKPGQGLEWIGYINPYNDGTKYNEKFKGKATLTSDKSSSTAYMELSSLTSEDSAVYYCGRHFDYYGRGYAVDYWGQGTSVTVSS (SEQ ID NO:22). In some embodiments, an antibody or antigen binding fragment thereof a comprises a complementarity determining region (CDR) having the amino acid sequence SNVMH (SEQ ID NO:30). In some embodiments, an antibody or antigen binding fragment thereof comprises a complementarity determining region (CDR) having the amino acid sequence YINPYNDGTKYNEKFKG (SEQ ID NO:32). In some embodiments, an antibody or antigen binding fragment thereof comprises a complementarity determining region (CDR) having the amino acid sequence HFDYYGRGYAVDY (SEQ ID NO:34).

In some embodiments of the present disclosure, an antibody, or antigen binding fragment thereof, is provided that comprises an amino acid sequence having at least 90% sequence identity to MDFQVQIISFMLISVTVMLSSGEIVLTQSPALMAASPGEKVTITCSVSSSISSSYLHWYQQRSETS PKPWIYGTSNLASGVPVRFSGNGSGTSYSLTISSMEAEDAATYYCQQWSSYPLTFGGGTKLEIK (SEQ ID NO:38). In some embodiments, an antibody or antigen binding fragment thereof comprises a complementarity determining region (CDR) having the amino acid sequence SVSSSISSSYLH (SEQ ID NO:46). In some embodiments, an antibody or antigen binding fragment thereof comprises a complementarity determining region (CDR) having the amino acid sequence GTSNLAS (SEQ ID NO:48). In some embodiments, an antibody or antigen binding fragment thereof of comprises a complementarity determining region (CDR) having the amino acid sequence QQWSSYPLT (SEQ ID NO:50).

In some embodiments, an antibody, or antigen binding fragment thereof, comprising an amino acid sequence having at least 90% sequence identity to MVSSAQFLGLLLLCFQGTRCDIQMTQTTSSLSASLGDRVTISCSASQDISNYLNWYQRKPDGTV KLLIYYTSSLHSGVPSRFSGSGSGTDYSLTISNLEPEDIATYYCLQYSKLPWTFGGGTKLEIK (SEQ ID NO:54). In some embodiments, an antibody or antigen binding fragment thereof comprises a complementarity determining region (CDR) having the amino acid sequence SASQDISNYLN (SEQ ID NO:62). In some embodiments, an antibody or antigen binding fragment thereof comprises a complementarity determining region (CDR) having the amino acid sequence YTSSLHS (SEQ ID NO:64). In some embodiments, an antibody or antigen binding fragment thereof comprises a complementarity determining region (CDR) having the amino acid sequence LQYSKLPWT (SEQ ID NO:66).

In some aspects of the present disclosure, a nucleic acid molecule is provided that comprises a nucleic acid sequence encoding any of the antibodies or antigen fragments thereof described herein.

In some embodiments, the NOHA antibody comprises a combination of heavy chain sequence(s) and light chain sequences(s) are as follows.

H1 heavy chain sequence alone
H2 heavy chain sequence alone
L1 light chain sequence alone
L2 light chain sequence alone
L1 light chain sequence; L2 light chain sequence combination
H1 heavy chain sequence; H2 heavy chain sequence combination
H1 heavy chain sequence; L1 light chain sequence combination
H1 heavy chain sequence; L2 light chain sequence combination
H1 heavy chain sequence; L1 light chain sequence; L2 light chain sequence combination
H1 heavy chain sequence; L2 light chain sequence; L1 light chain sequence combination
L1 light chain sequence; H1 heavy chain sequence; L2 light chain sequence combination
H2 heavy chain sequence; L1 light chain sequence combination
H2 heavy chain sequence; L2 light chain sequence combination
H2 heavy chain sequence; L1 light chain sequence; L2 light chain sequence combination
H2 heavy chain sequence; L2 light chain sequence; L1 light chain sequence combination
L1 light chain sequence; H2 heavy chain sequence; L2 light chain sequence combination
H1 heavy chain sequence; H2 heavy chain sequence; L1 light chain sequence combination
H2 heavy chain sequence; H1 heavy chain sequence; L1 light chain sequence combination
H1 heavy chain sequence; H2 heavy chain sequence; L2 light chain sequence combination
H2 heavy chain sequence; H1 heavy chain sequence; L2 light chain sequence combination
L2 light chain sequence; H1 heavy chain sequence; H2 heavy chain sequence; L1 light chain sequence combination
L2 light chain sequence; H2 heavy chain sequence; H1 heavy chain sequence; L1 light chain sequence combination
H1 heavy chain sequence; L2 light chain sequence; L1 light chain sequence; H2 heavy chain sequence combination
H1 heavy chain sequence; L1 light chain sequence; L2 light chain sequence; H2 heavy chain sequence combination
L2 light chain sequence; H1 heavy chain sequence; L1 light chain sequence; H2 heavy chain sequence combination
L1 light chain sequence; H1 heavy chain sequence; L2 light chain sequence; H2 heavy chain sequence combination
L2 light chain sequence; H2 heavy chain sequence; L1 light chain sequence; H1 heavy chain sequence combination
L1 light chain sequence; H2 heavy chain sequence; L2 light chain sequence; H1 heavy chain sequence combination
H1 heavy chain sequence; H2 heavy chain sequence; L1 light chain sequence; L2 light chain sequence combination H1 heavy chain sequence; H2 heavy chain sequence; L2 light chain sequence; L1 light chain sequence combination H2 heavy chain sequence; H1 heavy chain sequence; L1 light chain sequence; L2 light chain sequence combination H2 heavy chain sequence; H1 heavy chain sequence; L2 light chain sequence; L1 light chain sequence combination.

In some embodiments, the NOHA antibody comprises a combination of CDRs from the heavy chain sequence(s) and light chain sequences(s). For example, combinations of CDRs are as follows.

3 CDRs from the H1 heavy chain sequence alone

3 CDRs from the H2 heavy chain sequence alone

3 CDRs from the L1 light chain sequence alone

3 CDRs from the L2 light chain sequence alone

3 CDRs from the L1 light chain sequence; 3 CDRs from the L2 light chain sequence combination 3 CDRs from the H1 heavy chain sequence; 3 CDRs from the H2 heavy chain sequence combination 3 CDRs from the H1 heavy chain sequence; 3 CDRs from the L1 light chain sequence combination 3 CDRs from the H1 heavy chain sequence; 3 CDRs from the L2 light chain sequence combination 3 CDRs from the H1 heavy chain sequence; 3 CDRs from the L1 light chain sequence; 3 CDRs from the L2 light chain sequence combination 3 CDRs from the H1 heavy chain sequence; 3 CDRs from the L2 light chain sequence; 3 CDRs from the L1 light chain sequence combination 3 CDRs from the L1 light chain sequence; 3 CDRs from the H1 heavy chain sequence; 3 CDRs from the L2 light chain sequence combination 3 CDRs from the H2 heavy chain sequence; 3 CDRs from the L1 light chain sequence combination 3 CDRs from the H2 heavy chain sequence; 3 CDRs from the L2 light chain sequence combination 3 CDRs from the H2 heavy chain sequence; 3 CDRs from the L1 light chain sequence; 3 CDRs from the L2 light chain sequence combination 3 CDRs from the H2 heavy chain sequence; 3 CDRs from the L2 light chain sequence; 3 CDRs from the L1 light chain sequence combination 3 CDRs from the L1 light chain sequence; 3 CDRs from the H2 heavy chain sequence; 3 CDRs from the L2 light chain sequence combination 3 CDRs from the H1 heavy chain sequence; 3 CDRs from the H2 heavy chain sequence; 3 CDRs from the L1 light chain sequence combination 3 CDRs from the H2 heavy chain sequence; 3 CDRs from the H1 heavy chain sequence; 3 CDRs from the L1 light chain sequence combination 3 CDRs from the H1 heavy chain sequence; 3 CDRs from the H2 heavy chain sequence; 3 CDRs from the L2 light chain sequence combination 3 CDRs from the H2 heavy chain sequence; 3 CDRs from the H1 heavy chain sequence; 3 CDRs from the L2 light chain sequence combination 3 CDRs from the L2 light chain sequence; 3 CDRs from the H1 heavy chain sequence; 3 CDRs from the H2 heavy chain sequence; L1 light chain sequence combination 3 CDRs from the L2 light chain sequence; 3 CDRs from the H2 heavy chain sequence; 3 CDRs from the H1 heavy chain sequence; 3 CDRs from the L1 light chain sequence combination 3 CDRs from the H1 heavy chain sequence; 3 CDRs from the L2 light chain sequence; 3 CDRs from the L1 light chain sequence; 3 CDRs from the H2 heavy chain sequence combination 3 CDRs from the H1 heavy chain sequence; 3 CDRs from the L1 light chain sequence; 3 CDRs from the L2 light chain sequence; 3 CDRs from the H2 heavy chain sequence combination 3 CDRs from the L2 light chain sequence; 3 CDRs from the H1 heavy chain sequence; 3 CDRs from the L1 light chain sequence; 3 CDRs from the H2 heavy chain sequence combination 3 CDRs from the L1 light chain sequence; 3 CDRs from the H1 heavy chain sequence; 3 CDRs from the L2 light chain sequence; 3 CDRs from the H2 heavy chain sequence combination 3 CDRs from the L2 light chain sequence; 3 CDRs from the H2 heavy chain sequence; L1 light chain sequence; H1 heavy chain sequence combination L1 light chain sequence; H2 heavy chain sequence; L2 light chain sequence; 3 CDRs from the H1 heavy chain sequence combination 3 CDRs from the H1 heavy chain sequence; 3 CDRs from the H2 heavy chain sequence; 3 CDRs from the L1 light chain sequence; 3 CDRs from the L2 light chain sequence combination 3 CDRs from the H1 heavy chain sequence; 3 CDRs from the H2 heavy chain sequence; 3 CDRs from the L2 light chain sequence; 3 CDRs from the L1 light chain sequence combination 3 CDRs from the H2 heavy chain sequence; 3 CDRs from the H1 heavy chain sequence; 3 CDRs from the L1 light chain sequence; 3 CDRs from the L2 light chain sequence combination 3 CDRs from the H2 heavy chain sequence; 3 CDRs from the H1 heavy chain sequence; 3 CDRs from the L2 light chain sequence; 3 CDRs from the L1 light chain sequence combination.

In some embodiments, the antibody or antigen binding fragment thereof comprises at least three CDRs from Tables A-D. In some embodiments, the antibody or antigen binding fragment thereof comprises the three CDRs from Table A. In some embodiments, the antibody or antigen binding fragment thereof comprises the three CDRs from Table B. In some embodiments, the antibody or antigen binding fragment thereof comprises the three CDRs from Table C. In some embodiments, the antibody or antigen binding fragment thereof comprises the three CDRs from Table D. In some embodiments, the antibody comprises the three CDRs from Table A and three CDRs from Table C or D. In some embodiments, the antibody comprises the three CDRs from Table B and three CDRs from Table C or D. In some embodiments, the antibody comprises the six CDRs from Tables A and B and the six CDRs from Table C and D.

Alternative to the above-mentioned combinations that could occur via disulfide bonding between cysteine amino acid residues within these fragments, any generic polypeptide sequence can be attached to one or both ends of each of the two heavy chain region sequences (H1 and H2) and two light chain region sequences (L1 and L2), and linked together in any of the above-mentioned 32 combinations. This is an effective means to achieve binding selectivity and sensitivity to the NOHA biomarker.

Even a short segment of each of the two heavy chain region sequences (H1 and H2) and/or two light chain region sequences (L1 and L2), (for example one or more CDRs that specifically bind NOHA) could be flanked with any polypeptide sequence and linked together in any of the-above mentioned 32 combinations. This is also an effective means to achieve binding selectivity and sensitivity to the NOHA biomarker, that are comparable to the data shown in our study.

Compositions and Kits

Compositions and kits for detecting NOHA and diagnosing or monitoring ER− ovarian cancer or breast cancer are also provided. In some embodiments, a composition is provided that includes an agent that recognizes NOHA. In some embodiments, a kit is provided that includes an agent that recognizes NOHA. In some embodiments, the compositions and kits of the present disclosure can include one or more NOHA antibodies, or antigen binding fragments thereof, for use in connection with an immunoassay such as immunohistochemistry or ELISA or Western blot.

In some embodiments, the kit comprises a solid support, such as a chip, a microtiter plate, or a bead or resin having capture reagents attached thereon, wherein the capture reagents bind NOHA. Thus, for example, the kits of the present invention can comprise mass spectrometry probes for Surface-enhanced laser desorption/ionization (SELDI), such as ProteinChip® arrays. In the case of biospecfic capture reagents, the kit can comprise a solid support with a reactive surface, and a container comprising the biospecific capture reagents.

In some embodiments, the kit also comprises a washing solution or instructions for making a washing solution, in which the combination of the capture reagent and the washing solution allows capture of the biomarker or biomarkers (e.g., NOHA) on the solid support for subsequent detection by, e.g., mass spectrometry. The kit may include more than type of adsorbent, each present on a different solid support.

In a further embodiment, the kit comprises instructions for use in any of the methods described herein. In embodiments, the instructions provide suitable operational parameters in the form of a label or separate insert. For example, the instructions may inform a consumer about how to collect the sample, how to wash the probe, or the particular biomarkers to be detected.

A control sample can additionally be included in the kit, wherein a difference in the test sample compared to the control sample indicates a status of ER− breast or ovarian cancer. The change can be more than about 10%, more than about 20%, more than about 30%, more than about 50%, more than about 60%, more than about 80%, more than about 100%, or more, or any number therebetween. In some embodiments, the control sample is indicative of a healthy individual, or an individual having ER− tumor of one or more grades and severities. In some embodiments, the control may include controls for different ethnic backgrounds.

The compositions and methods of the present disclosure are described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1

Plasma samples from ER−/ER+ ovarian and breast cancer patients, categorized as low-grade tumor, were assessed for NOHA levels. Three-dimensional (3D) spheroids of ER− and ER+ primary cells from breast cancer and ovarian cancer patients, along with control/healthy cells, were cultured in medium between weeks 1 and 9, and tested for cell proliferation and cell cycle by Guave-8HT® flow cytometry (Millipore, MA) using kit assays. Inducible nitric-oxide synthase (NOS2) expression was determined by ELISA kit assay (Bioassay systems, CA); and cellular nitric-oxide as total nitrite was determined by calorimetric assay (Cayman Chemicals, IL). Extracellular concentrations of Nw-hydroxy-L-Arginine (NOHA) in the culture medium, and cellular L-Arginine were determined by LC-MS assay. Statistical significance was set at $p<0.01$.

Human origin cell lines of Caucasian origin for ER− ovarian cancer (i.e., UWB1.289), ER− breast cancer (i.e., MDA-MB436), ER+ ovarian cancer (i.e., OVCAR3), and ER+ breast cancer (i.e. MCF7), were obtained from American type culture collection (Manassas, Va.). All cells were cultured to 80% confluence in T75 flasks with enriched Dulbecco's minimal eagle medium (viz., DMEM medium; containing 11% fetal bovine serum, 2 mM glutamine, 100 Units/ml penicillin, and 100 µg/ml streptomycin) for 1 week at 37° C. and 5% CO2. The cell monolayer was washed twice with 5 ml/wash 1× phosphate buffered saline (PBS), and incubated with 1 ml of 0.25% trypsin EDTA for 2-3 min in 37° C. incubator to detach the cells from their monolayer. The detached cells were neutralized with 1 ml of DMEM, centrifuged (at 300 g for 6 min), washed twice with 1 ml/wash 1×PBS, and re-suspended in 0.5 ml DMEM medium containing for 3D spheroid culture development.

For 3D spheroid development, 300 µl of confluent cell suspensions (of ER−, ER+, and control) for both ovarian carcinoma and breast cancer were mixed with 30 µl of 1× spheroid formation medium containing extracellular matrix proteins (Cultrex, Gaithersburg, Md.), and were plated (in triplicate) on InSphero GravityPLUS™ hanging drop 96-well plate system (PerkinElmer, Hopkinton, Mass.) at 60 µl/well (with a final cell count of about 1×10$^4$ cells/well) to stimulate spontaneous formation of a single spheroid of cells within 24 h at 37° C. and 5% CO2 incubation. The culture medium was changed daily and collected weekly for 9 weeks longitudinally for determining NOHA levels by LC-MS. 3D spheroid growth (during the 10-week culture period) was assessed by high-content imaging system (Perkin Elmer, Waltham, Mass.) using a 2× objective lens, and tumor size was determined using Harmony® software (Perkin Elmer) for 9 weeks. Those 3D-spheroids with volume ≤250 µm and with characteristic similarity to control healthy cells were considered "low-grade," and 3D spheroids with volume ≥400 µm and with less similarity to control spheroids were considered "intermediate-to-high grade".

To prepare 3D spheroid lysates at the end of each week, and up to 9 weeks, 3D-spheroids were lysed by washing them with 500 µl 1×PBS twice and incubated in 250 µl 0.25% trypsin-EDTA for 1-3 min at 37° C. and 5% CO2 with gentle horizontal shaking to dislodge spheroids into cell suspension. After 20 µl of the cell suspension was used to test cell viability using ViaCount® kit (Millipore, MA), using Guava 8HT flow cytometer (Millipore, MA), the spheroid cell suspension was centrifuged at 300×g for 5 min, and the resultant cell pellet was treated with 500 µl ice-cold lysis buffer (containing 20 mM Tris, pH 7.5; 150 mM NaCl; 1% Triton X-100; 2.5 mM sodium pyrophosphate, 1 mM ß-glycerophosphate; 1 mM phenylmethylsulfonyl fluoride) at 2-8° C., for 5 min. The content was then vortexed for 2 min and centrifuged at 14,000×g for 5 min at 2-4° C. 400 µl of the final cell lysate supernatant was collected for metabolite assessment. L-Arginine and NOHA levels were measured in medium and in cell lysate by LC-MS assay. NOS2 expression and nitric oxide levels were determined from commercial kit assays.

Figure 2A:
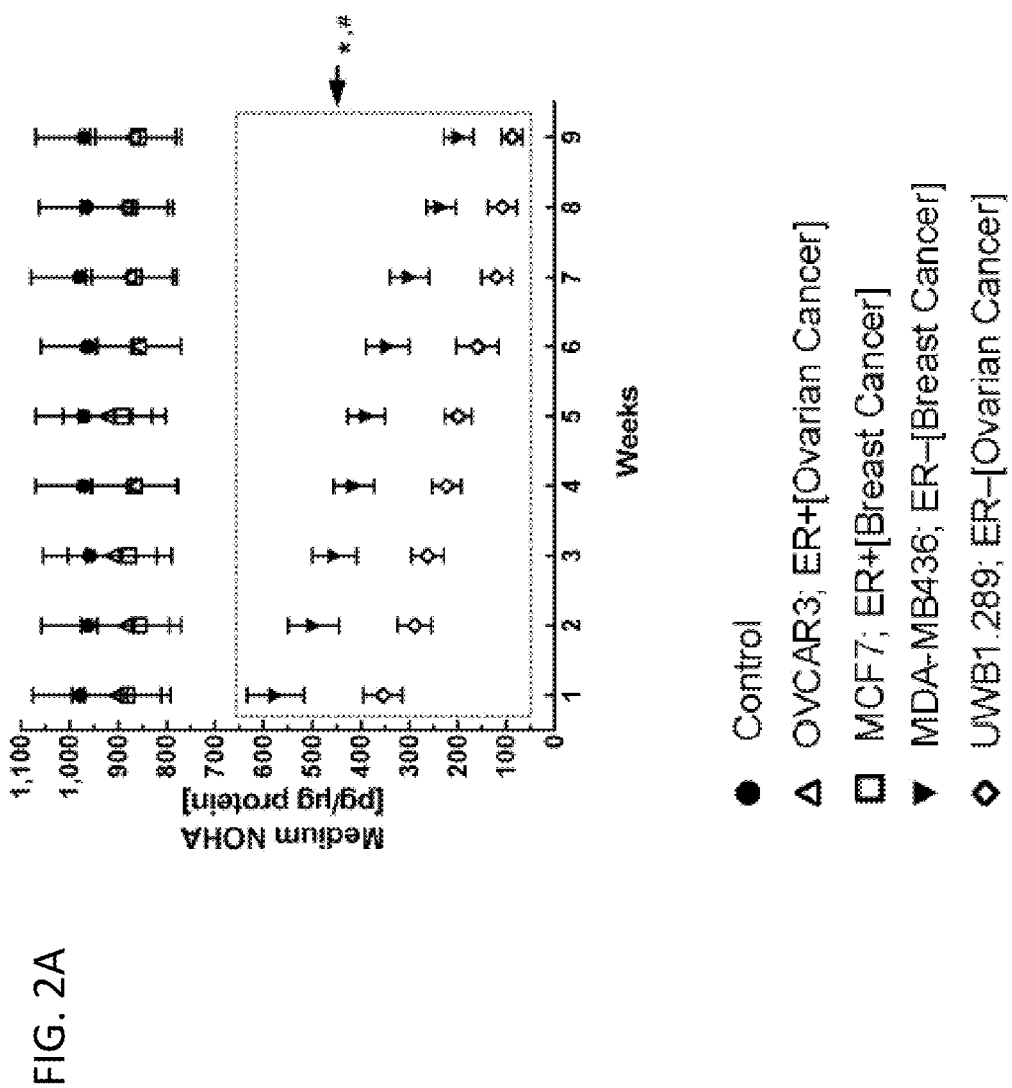
FIGS. 2A-2D illustrate NOHA's predictive assessment between ER−/ER+ ovarian carcinoma and breast cancer.
Figure 2B:
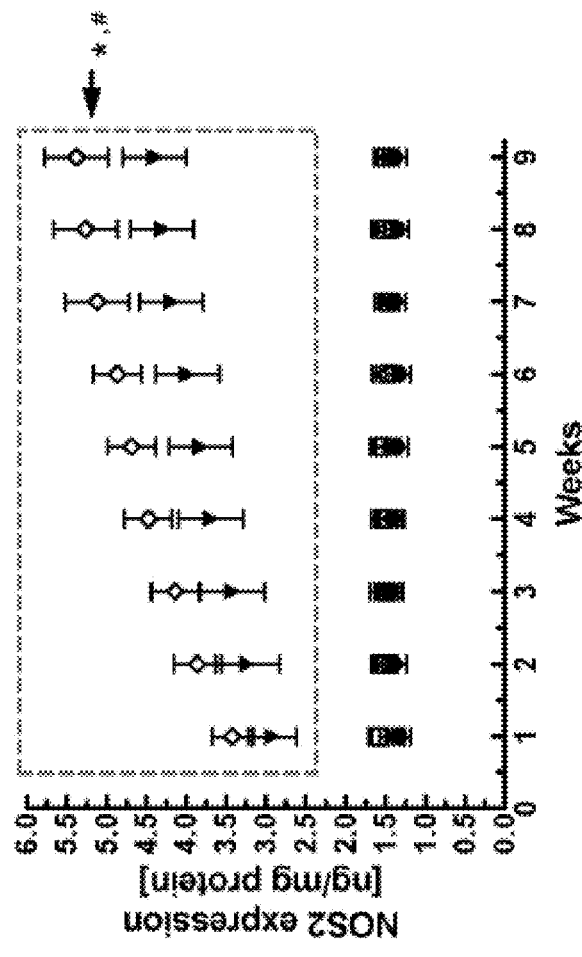
Figure 2C:
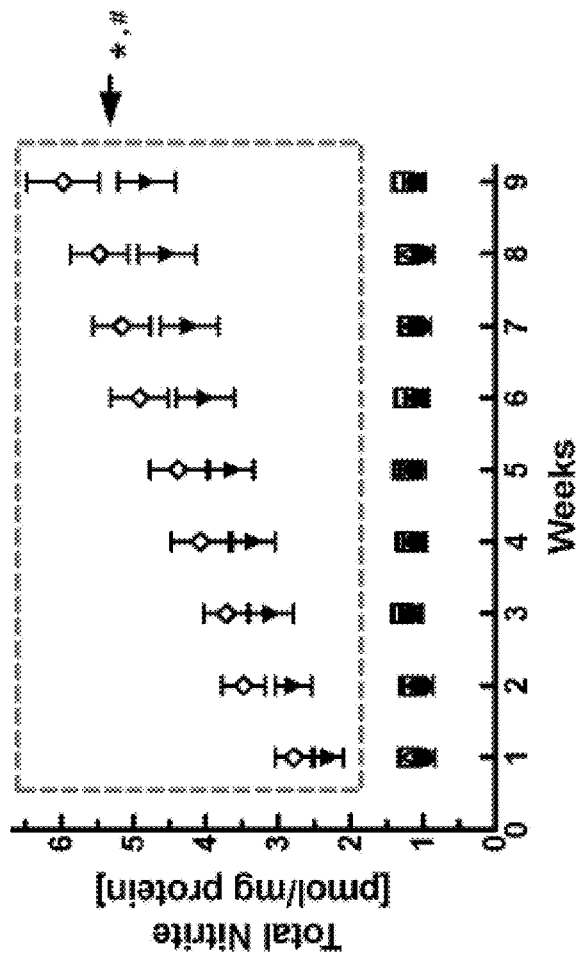
Figure 2D:
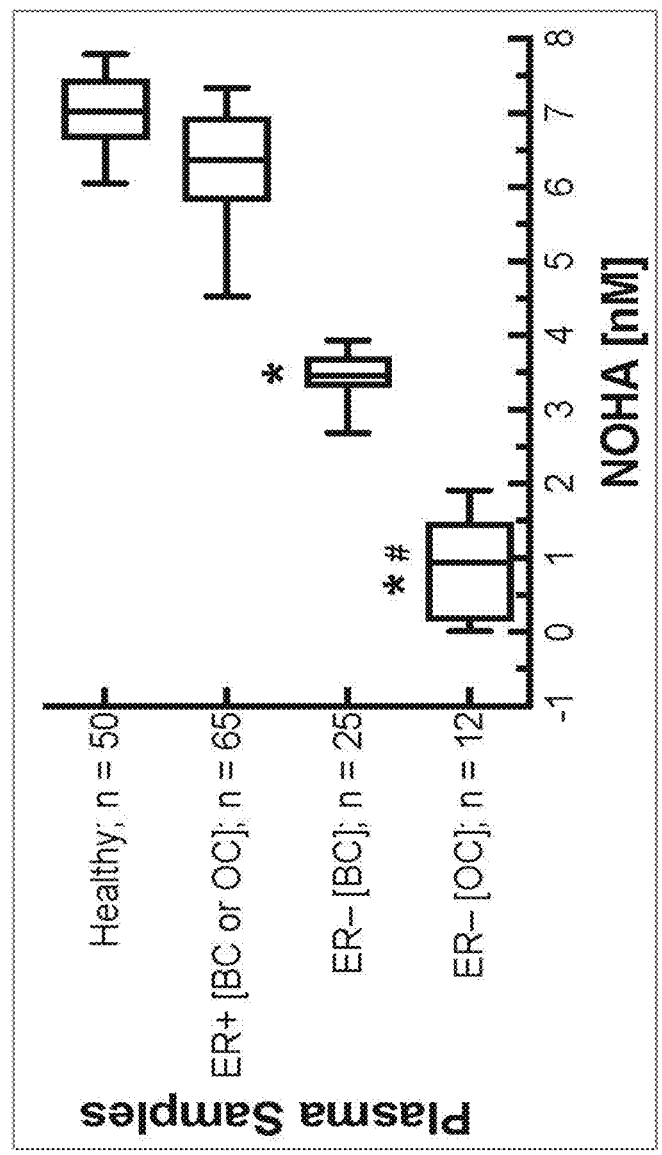

Among ER− and ER+ ovarian and breast cancer patients, a plasma NOHA reduction of ≥33.9% was seen in only ER− cancer patient plasma samples (FIG. 1). This ER− tumor selective reduction in plasma NOHA allowed for distinguishing ER− ovarian cancer and ER− breast cancer subtypes, with a ≥48.8% greater NOHA reduction in ER− ovarian tumors than observed with ER− breast cancer (FIG. 2D). In 3D-spheroids, a progressive reduction of ≥1-fold for NOHA in extracellular medium of ER− 3D-spheroids (during 9-week culture), along with a progressive increase in cellular NOS2 and nitric-oxide levels by ≥1-fold was observed, compared to those in ER+ and control 3D-spheroids ($p<0.01$, n=6; FIGS. 2A-2C). ER− ovarian cancer 3D-spheroids had reduced NOHA level of ≥38.9% than that in ER− breast cancer 3D-spheroids, over 9-weeks. The distinction in extracellular NOHA reduction, between ER− ovarian and ER− breast tumor 3D spheroids, correlated with their respective 3D spheroid tumor grades. The cellular NOS2 expression and nitric-oxide levels in ER− ovarian cancer 3D-spheroids were also elevated by ≥17.4% and ≥18.8%, respectively than those seen in ER− breast cancer 3D-spheroids during the 9-week incubation period.

Figure 3:
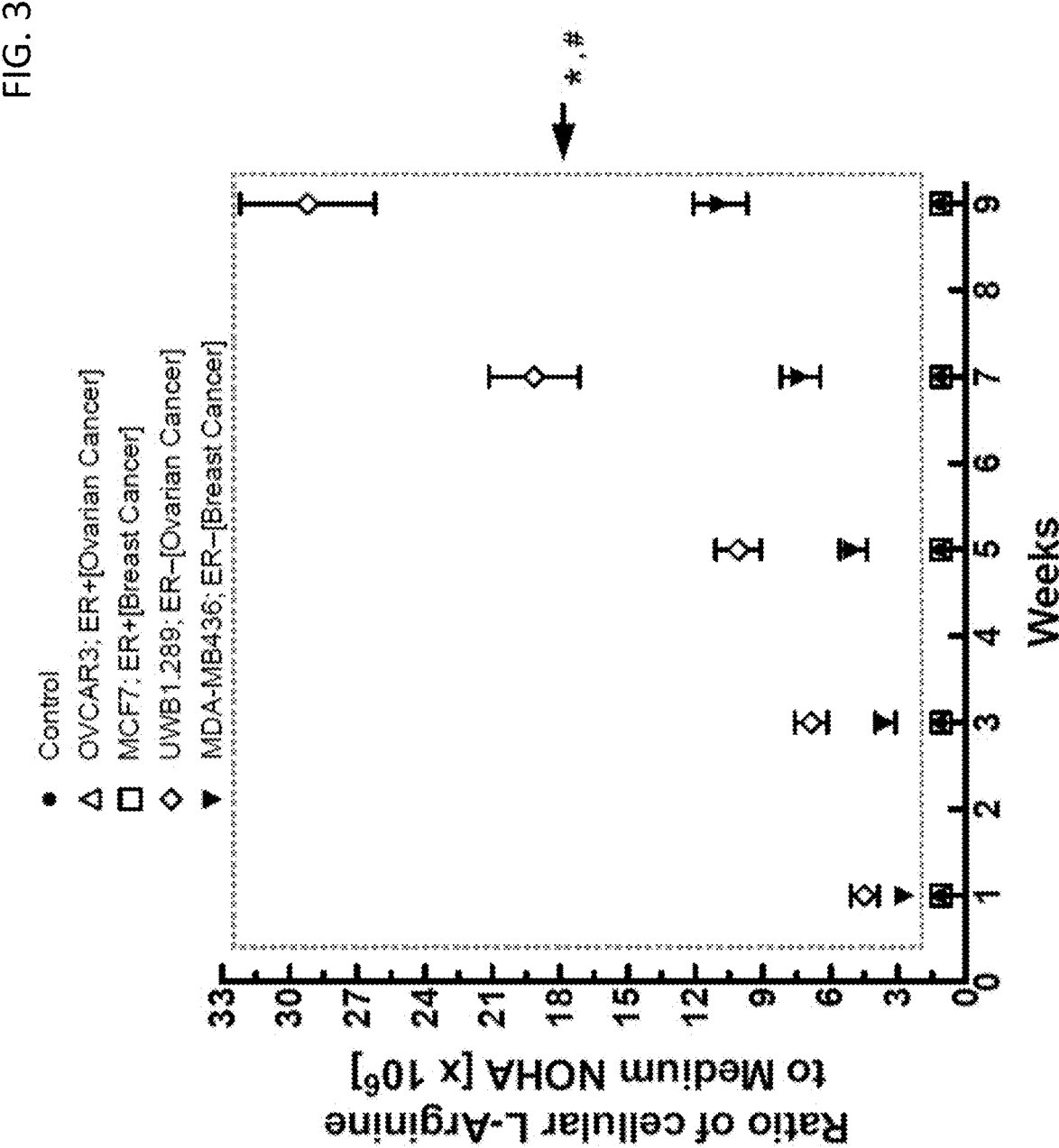
FIG. 3 compares cellular L-Arginine availability to medium NOHA in ER−/ER+ breast and ovarian cancer. The data inside the dotted square showed statistical significance in the ER− group versus ER+ or control ($p<0.01$) and between ER− ovarian and ER− breast cancer ($p<0.01$, n=6).

NOHA predictive assessment between ER− and ER+ ovarian carcinoma and breast cancer 3D spheroids cultured over 9 weeks was performed. As shown in FIG. 3, the ratio of L-Arginine to NOHA increased substantially in ER− ovarian cancer spheroids, and to a lesser extent in ER− breast cancer spheroids, during the 9 weeks. No significant difference in the ratio of L-Arginine to NOHA was observed in ER+ breast or ER+ ovarian cancer compared to controls.

Figure 4:
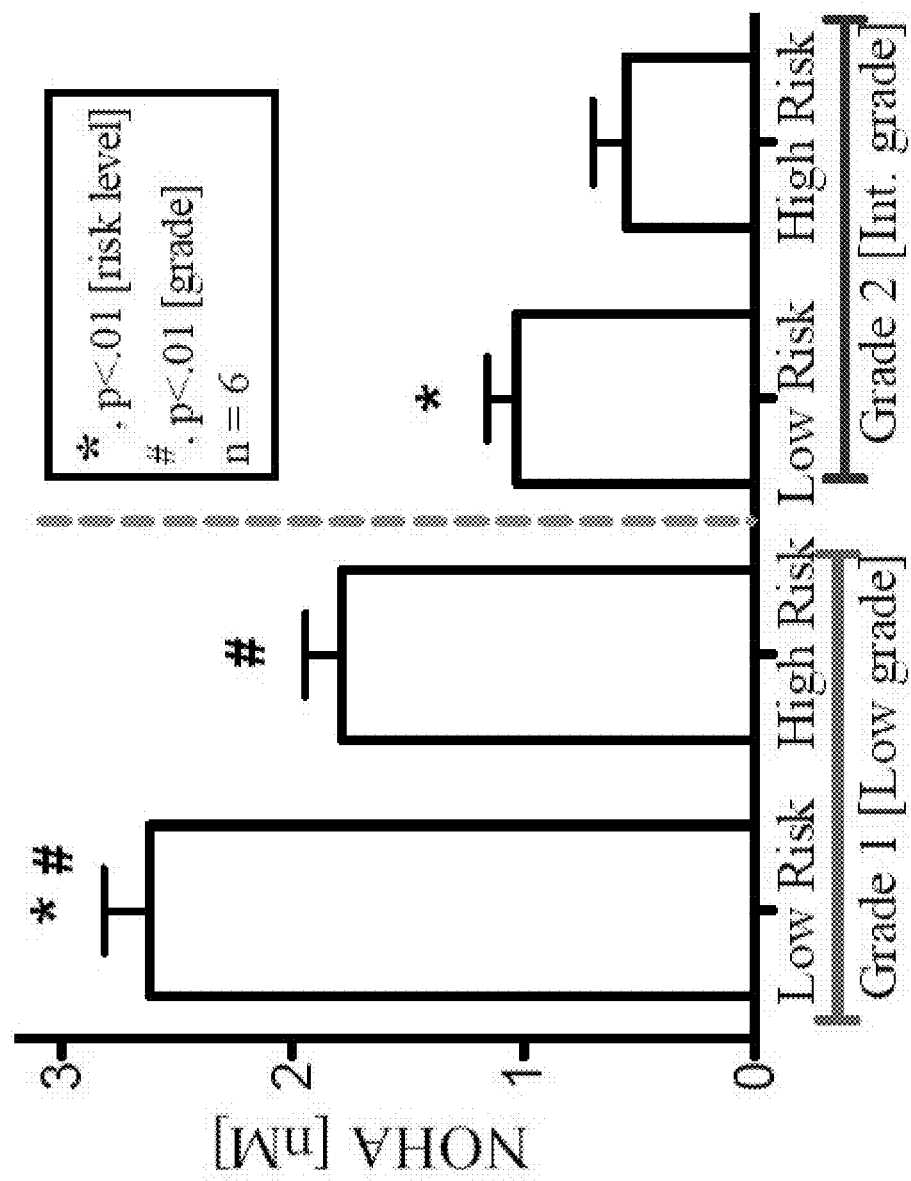
FIG. 4 shows NOHA's correlation with molecular phenotype (based on MammaPrint) and disease grade in ER− cases.
Figure 6A:
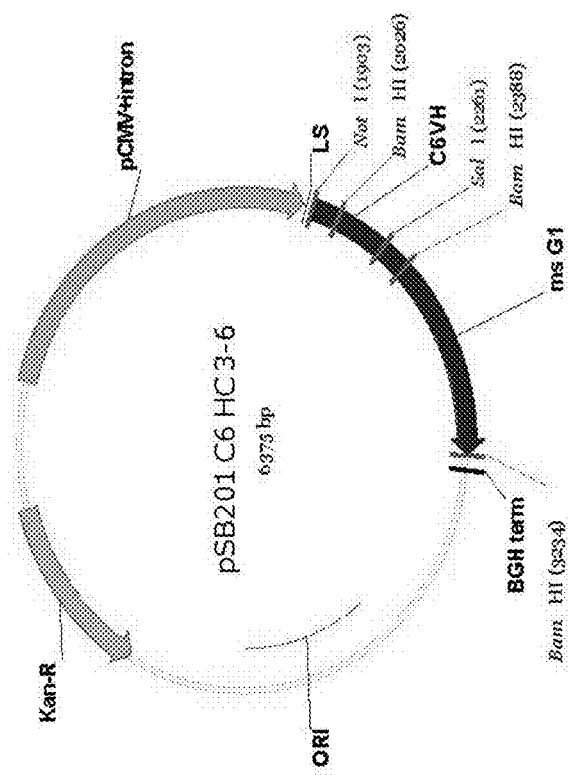
FIGS. 6A-6D provide block maps of the exemplary plasmids.
Figure 6B:
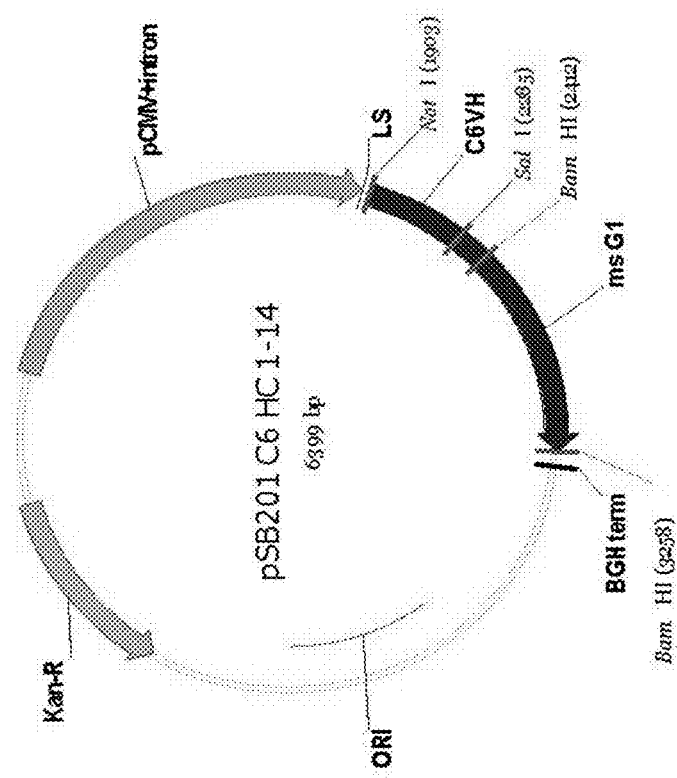
Figure 6C:
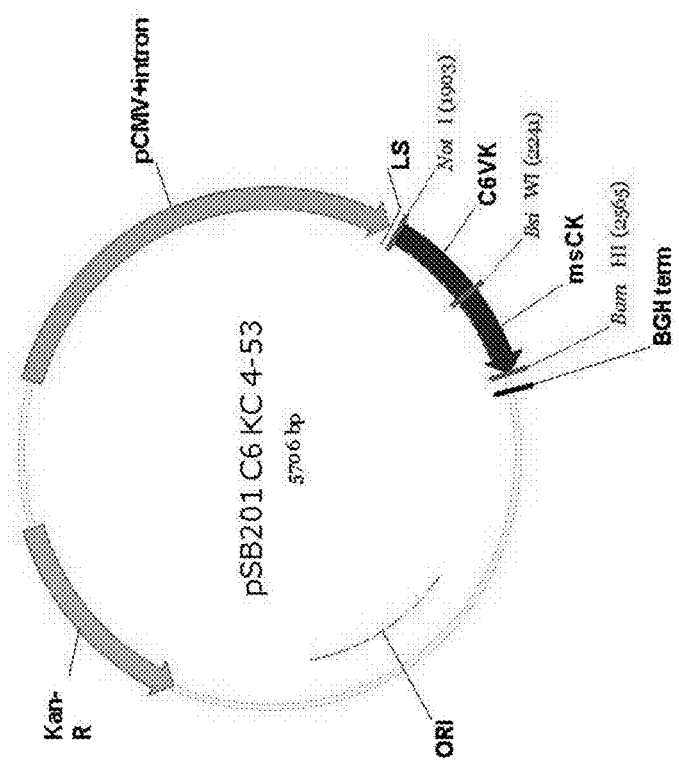
Figure 6D:
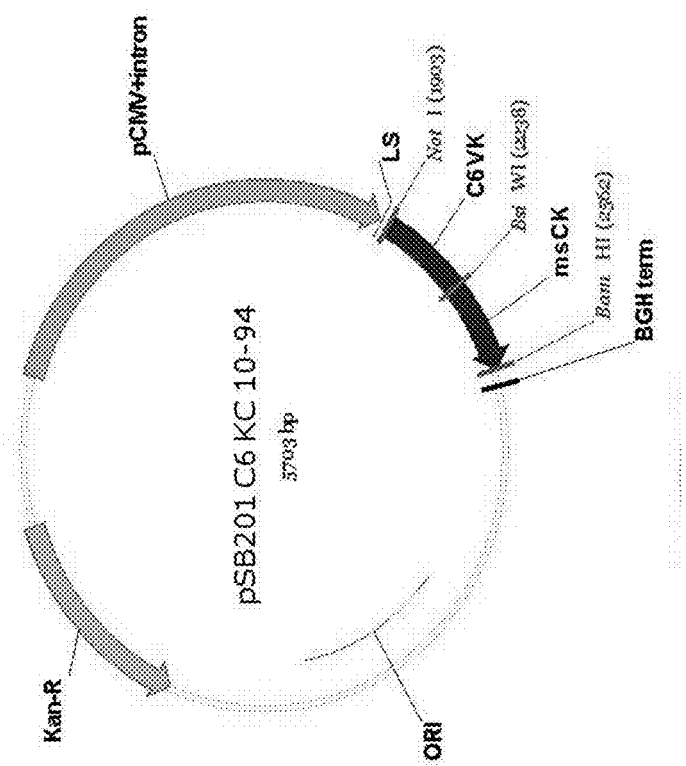

In clinical studies, ER− selective NOHA reduction in the circulation appeared to correlate with molecular phenotype (i.e., genomic profile based on MammaPrint®) and disease grade, thereby differentiating high-risk from low-risk ER− cases (FIG. 4). These data show NOHA's role as a biomarker in breast cancer personalized medicine. This is particularly relevant in low-resource settings where access to pathology services/molecular diagnostics is limited to non-existent as well as in the U.S. where efforts are focused on promoting healthcare value (i.e., NOHA assay costs are ~$19).

Referring to FIG. 5, no significant reduction in percent NOHA recovery was observed after 21 days at ≤25 C. NOHA can maintain its stability for 7-days in fresh plasma samples stored at temperature below 4° C. NOHA measurements from dried plasma samples are concordant with results from fresh plasma and remain stable and sensitive at a wider temperature range (i.e., between −80° C. to 42° C.) for at least 14 days (FIG. 5). The dried plasma assay simplifies sample collection and shipment for analysis, thereby serving as an accessible and cost-effective diagnostic biomarker. In comparison to IHC testing ($90.07-$118 in the U.S. and €68.69 in Europe), the cost of NOHA measurement by LC-MS is only $19.34/patient sample (U.S.) (including supplies, sample processing, data analysis, and technician time), with a short turnaround time of ≤1 hour/sample. NOHA analysis using dried plasma holds promise in the low-resource setting where access to IHC is limited by cost/dependence on perishable reagents and lack of pathologists to interpret results. As NOHA testing is not reliant on expensive equipment or reagents, nor is its interpretation dependent on pathologists, it could be readily available regionally in low-resource settings, thus, greatly improving access to optimized hormone therapy.

NOHA Antibody Hybridoma Sequencing:

Leader peptide and variable regions of the immunoglobulin gene transcripts expressed in hybridoma FO cells were amplified from isolated mRNA using RT-PCR protocol and sequenced using a standard dye-terminator capillary sequencing method.

Method:

Leader peptide and variable regions of the immunoglobulin gene transcripts expressed by the submitted hybridoma samples were amplified with sets of proprietary primers from mRNA isolated from the received samples using our standard RT-PCR protocol and sequenced using a standard dye-terminator capillary sequencing method. The identified regions were flanked for seamless cloning into mammalian expression vectors encoding the mouse kappa or gammal constant regions.

A. RT-PCR Protocol

1. Prepare the RNA/primer mixture for each tube:

| | |
|---|---|
| Total RNA | 5 µg |
| Random hexamers (50 ng/µl) 3 µl | 3 µl |
| 10 mM dNTP mix | 1 µl |
| DEPC $H_2O$ | to 10 µl |

2. Incubate the samples at 65° C. for 5 min and then on ice for at least 1 min.
3. Prepare reaction master mixture. For each reaction:

| | |
|---|---|
| 10x RT buffer | 2 µl |
| 25 mM $MgCl_2$ | 4 µl |
| 0.1M DTT | 2 µl |
| RNAaseOUT | 1 µl |

4. Add the reaction mixture to the RNA/primer mixture, mix briefly, and then place at room temperature for 2 min.
5. Add 1 µl (50 units) of SuperScript II RT to each tube, mix and incubate at 25° C. for 10 min.
6. Incubate the tubes 42° C. for 50 min, heat inactivate at 70° C. for 15 min, and then chill on ice.
7. Add 1 µl RNase H and incubate at 37° C. for 20 min.
8. Normalize the primer concentrations and mix gene-specific forward and reverse primer pair. Each primer (forward or reverse) concentration in the mixture is 5 pmol/µl.
9. Set up the following PCR cycle:
   50° C. for 2 min;
   95° C. for 10 min
   40 cycles of 95° C. 15 s; 60° C. 30 s; and 72° C. 30 s; and
   72° C. 10 min
10. A real time PCR reaction mixture can be either 50 µl or 25 µl. Prepare the following mixture in each optical tube.

| | |
|---|---|
| 25 μl SYBR Green Mix (2x) | OR 12.5 μl SYBR Green Mix (2x) |
| 0.5 μl liver cDNA | 0.2 μl liver cDNA |
| 2 μl primer pair mix (5 pmol/μl each primer) | 1 μl primer pair mix (5 pmol/μl each primer) |
| 22.5 μl H$_2$O | 11.3 μl H$_2$O |

11. After PCR is finished, remove the tubes from the machine. The PCR specificity is examined by 3% agarose gel using 5 μl from each reaction.
12. Analyze the real-time PCR result to determine if there is a bimodal dissociation curve or abnormal amplification plot.

B. Dye-Terminator Capillary Sequencing Method

Dye-labeled terminator cycle sequencing with d-rhodamine and BigDye terminators was performed using AmpliTaq DNA polymerase and 100 μM dNTPs. The concentrations of the terminators used in the reactions were determined by titrating each terminator in single-color terminator reactions and selecting the concentration which maximized the signal. The concentrations were adjusted according to the relative brightness of each dye in order to obtain approximately equivalent signal for each color in the four-color reaction.

Results:

Annotated sequence of the identified leader sequences for the variable regions (LS-VRs):

```
LOCUS   C6_VH3-6_G1    396 bp DNA linear 10-OCT-2018
FEATURES Location/Qualifiers
  J_segment    364..396
    /label=JH
  V_segment    349..363
    /label=CDR3
  V_region     253..348
    /label=FWR3
  V_segment    205..252
    /label=CDR2
  V_region     163..204
    /label=FWR2
  V_segment    145..162
    /label=CDR1
  V_region     55..144
    /label=FWR1
  sig_peptide 1..54
    /label=LS
  CDS  1..392
    /label=LS-VH
  /translation="MMVLSLLYLLTAIPGILSDVQLQESGPGLVKPSQSLSLTCSVT

GYSITSGYYWNWIRQFPGNKLEWMGYTNYDGSNNYNPSLKNRISITRDTS

K NQFFLKLNSVTTEDTGTYYCAGPYLDYWGQGTTLTVSS" (SEQ ID

NO:6)

BASE COUNT  100 a 109 c 81 g  106 t
ORIGIN 1 atgatggtgt taagtcttct gtacctgttg acagccattc ctggtatcct gtctgatgta 61 cagcttcagg agtcaggacc tggcctcgtg aaaccttctc agtctctgtc tctcacctgc 121 tctgtcactg gctactccat caccagtggt tattactgga actggatccg gcagtttcca 181 ggaaacaaac tggaatggat gggctacaca aactacgacg gtagcaataa ctacaaccca 241 tctctcaaaa atcgaatctc catcactcgt gacacatcta agaaccagtt tttcctgaag 301 ttgaattctg tgactactga ggacacaggt acatattact gtgcgggacc ctaccttgac 361 tactggggcc aaggcaccac tctcacagtc tcctca (SEQ ID NO:4)

LOCUS   C6_VH-14_G2a    423 bp DNA linear 10-OCT-2018
FEATURES   Location/Qualifiers
  J_segment    391..423
    /label=JH
  V_segment    352..390
    /label=CDR3
  V_region     256..351
    /la bel=FWR3
  V_segment    205..255
    /label=CDR2
  V_region     163..204
    /la bel=FWR2
  V_segment    148..162
    /label=2CDR1
  V_region     58..147
    /label=FWR1
  sig_peptide 1..57
    /label=LS
```

```
CDS 1..423
  /label=LS-VH
  /translation="MEWSGIFLFLLSGTAGVHFEVQLQQSGPELVKPGASVKMS

CKASGYKFTSNVMHWVKQKPGQGLEWIGYINPYNDGTKYNEKFKGKAT

LTSDKS SSTAYM ELSSL TSEDSAVYYCG RH

FDYYGRGYAVDYWGQGTSVTVSS" (SEQ ID NO:22)
BASE COUNT 106 a 98 c 114 g 105 t
ORIGIN 1 atggaatgga gcgggatctt tctctttctc ctgtcaggaa ctgcaggtgt ccactttgag 61 gtccagctgc agcagtctgg acctgagctg gtaaagcctg gggcttcagt gaagatgtcc 121 tgcaaggctt ctggatacaa attcactagc aatgttatgc actgggtgaa gcagaagcct 181 gggcagggcc ttgagtggat tggatatatt aatccttaca atgatggtac taagtacaat 241 gagaagttca aaggcaaggc cacactgact tcagacaaat cctccagcac agcctacatg 301 gagctcagca gcctgacctc tgaggactct gcggtctatt actgtgtgaag acattttgat 361 tactacggta ggggctacgc tgtggactac tggggtcaag gaacctcagt caccgtctcc 421 tca (SEQ ID NO:20)

LOCUS C6_VK4-53 390 bp DNA linear 10-OCT-2018
FEATURES Location/Qualifiers
  J_segment 361..390
    /label=JK
  V_segment 334..360
    /label=CDR3
  V_region 238..333
    /label=FWR3
  V_segment 217..237
    /label=CDR2
  V_region 172..216
    /label=FWR2
  V_segment 136..171
    /label=CDR1
  V_region 67..135
    /label=FWR1
  sig_peptide 1..66
    /label=LS
CDS 1..390
  /label=LS-VK
  /translation="MDFQVQIISFMLISVTVMLSSGEIVLTQSPALMAASPGEK

VTITCSVSSSISSSYLHWYQQRSETSPKPWIYGTSNLASGVPVRFSGNGSGT

SY SLTISSM EAEDAATYYCQQWSSYPLTFGG GTKLEI K"(SEQ ID

NO: 38)

BASE COUNT 101 a 100 c 92 g 97 t
ORIGIN 1 atggattttc aggtgcagat tatcagcttc atgctaatca gtgtcacagt catgttgtcc 61 agtggagaaa ttgtgctcac acagtctcca gcactcatgg ctgcatctcc aggggagaag 121 gtcaccatca cctgcagtgt cagctcaagt ataagttcca gctacttaca ctggtaccag 181 cagaggtcag aaacctcccc caaaccctgg atttatggca catccaacct ggcttctgga 241 gtccctgttc gcttcagtgg caatggatct gggacctctt attctctcac aataagcagc 301 atggaggctg aagatgctgc cacttattac tgtcaacagt ggagtagtta cccactcacg 361 ttcggagggg ggaccaagct ggaaataaaa (SEQ ID NO:36)

LOCUS C6_VK4-53 381 bp DNA linear 10-OCT-2018
FEATURES Location/Qualifiers
  J_segment 352..381
    /label=JK
  V_segment 325..351
```

```
       /label=CDR3
   V_region 229..324
       /label=FWR3
   V_segment 208..228
       /label=CDR2
   V_region 163..207
       /label=FWR2
   V_segment 130..162
       /label=CDR1
   V_region 61..129
       /label=FWR1
   sig_peptide 1..60
       /label=LS
   CDS 1..381
       /label=LS-VK
       /translation="MVSSAQFLGLLLLCFQGTRCDIQMTQTTSSLSASLGD

RVTISCSASQDISNYLNVVYQRKPDGTVKLLIYYTSSLHSGVPSRFS

GSGSGTDYSLTISNLEPEDIATYYCLQYSKLPWTFGGGTKLEIK"

(SEQ ID NO:54)

BASE COUNT   101 a   92 c   84 g   104 t
ORIGIN 1 atggtgtcct cagctcagtt ccttggtctc ctgttgctct gttttcaagg taccagatgt 61 gatatccaga tgacacagac tacatcctcc ctgtctgcct ctctgggaga cagagtcacc 121 atcagttgca gtgcaagtca ggacattagc aattatttaa actggtatca acggaaacca 181 gatggaactg ttaaactcct gatctattac acatcaagtt tacactcagg agtcccatca 241 aggttcagtg gcagtgggtc tgggacagat tattctctca ccatcagcaa cctggaacct 301 gaagatattg ccacttacta ttgtctgcag tatagtaagc ttccgtggac gttcggtgga 361 ggcaccaagc tggaaatcaa a (SEQ ID NO:52)
```

Block maps of the generated plasmids are presented in FIG. 6.

Example 2: ELISA Assay

To perform an ELISA assay to detect NOHA, monoclonal NOHA antibody (mAB) was mixed with NOHA antigen at varying concentrations of mAB or NOHA and incubated for 2 hours at 25° C. to allow antibody binding. BSA-NOHA ELISA strips were washed at least 3 times with 200 µl of 1× wash buffer (PBS, 0.025% Tween 10, 0.002% Zwitterion 3-14, pH 6.8-7). 100 µl of each mAB-NOHA complex was loaded to the ELISA Strip wells and incubated for 1 hour, at 25° C. After incubation, wells were decanted and washed with 200 µl of 1× wash buffer at least 8 times before adding 100 µl polyclonal HL-HRP conjugate (at 1:20,000 dilution). The wells were decanted and washed with 200 µl of 1× wash buffer at least 8 times before adding 100 µl of TMB substrate. The wells were incubated for 10 minutes in dark conditions and the horse radish peroxidase (HRP)-substrate reaction was stopped with 100 µl 0.1 N HCl. ELISA wells were read for absorbance at 450 nm using a VersaMax® Spectrophotometer (Molecular Devices, NH).

Figure 7:
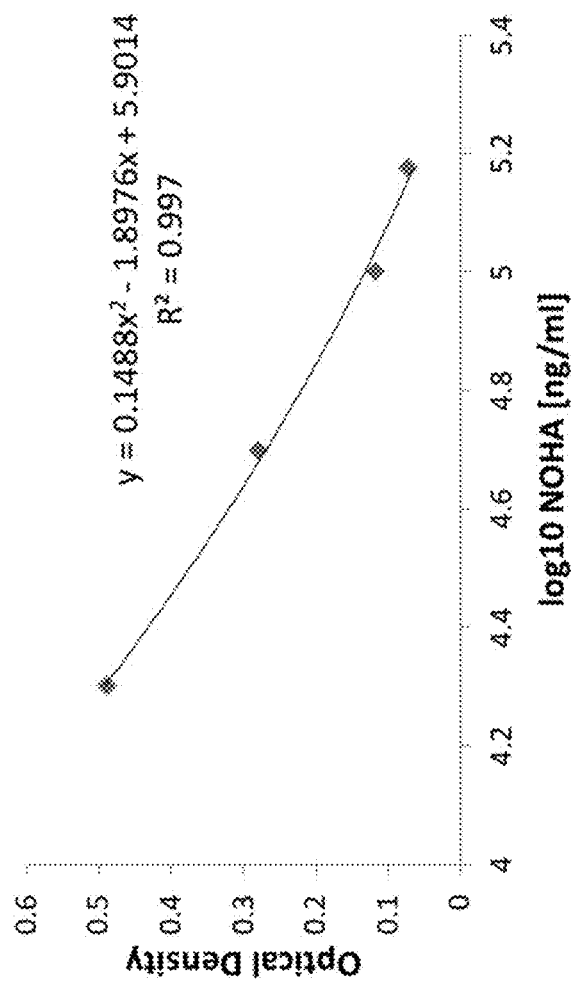
FIG. 7 provides an ELISA standard curve showing detection of the NOHA antigen with an antibody of the present disclosure.

For standard curve fitting (Table, 2; FIG. 7) the NOHA antigen of 150-0 ng/ml with 5 ng/ml mAB was used. The O.D. values (Y-axis) were plotted against the log NOHA antigen standard concentrations (X-axis) as an XY scatter plot. A polynomial order-2 trendline and R-squared confidence value were added.

TABLE 1

Monoclonal NOHA antibody (mAB) sensitivity assessment based to NOHA antigen availability

| In well concentration after 1:1 mix of reagents | | | Optical Density |
|---|---|---|---|
| NOHA (ng/ml) | mAB (ng/ml) | In well Ratio | (O.D) |
| 300 | 10 | 30:1 | 0.08* |
| 200 | 10 | 20:1 | 0.08* |
| 100 | 10 | 10:1 | 0.24 |
| 50 | 10 | 5:1 | 0.40 |
| 20 | 10 | 2:1 | 0.64 |
| 10 | 10 | 1:1 | 0.76 |
| 5 | 10 | 1:2 | 0.81 |
| 2.5 | 10 | 1:4 | 0.89 |
| 1 | 10 | 1:10 | 0.96 |
| 0 | 0 | Blank | 0.07 |

*represent significant concertation ratio to achieve complete mAB-NOHA complexation, resulting in negligible mAB binding to BSA-NOHA in ELISA strip wells.

TABLE 2

ELISA standard curve for NOHA antigen measurement.

| NOHA in well concentration (ng/ml) + 5 ng/ml of mAB | Log10 NOHA | Optical Density (O.D) |
|---|---|---|
| 150 | 5.176091 | 0.0717 |
| 100 | 5 | 0.1185 |

TABLE 2-continued

ELISA standard curve for NOHA antigen measurement.

| NOHA in well concentration (ng/ml) + 5 ng/ml of mAB | Log10 NOHA | Optical Density (O.D) |
|---|---|---|
| 50 | 4.69897 | 0.2782 |
| 20 | 4.30103 | 0.4895 |
| 10 | 4 | 0.6264 |
| 0 | NA | 1.4864 |

NA represents not available/calculatable data

TABLE 3A

Table 3. Identifying monoclonal NOHA antibody (mAB) lowest concentration range for ELISA assay.

| In well concentration after 1:1 mix of reagents | | | Optical Density |
|---|---|---|---|
| NOHA (ng/ml) | mAB (ng/ml) | In-well Ratio | (O.D) |
| 20 | 10 | 2:1 | 0.61 |
| 16 | 8 | 2:1 | 0.67 |
| 8 | 4 | 2:1 | 0.59 |
| 4 | 2 | 2:1 | 0.63 |
| 2 | 1* | 2:1 | 0.58* |
| 1.6 | 0.8 | 2:1 | 0.08 |
| 0.8 | 0.4 | 2:1 | 0.07 |
| 0 | 0 | Blank | 0.07 |

*represents the lowest effective mAB concentration, to achieve complexation with NOHA antigen, at different mAB-NOHA ratios.

TABLE 3B

| In well concentration after 1:1 mix of reagents | | | Optical Density |
|---|---|---|---|
| NOHA (ng/ml) | mAB (ng/ml) | In-well Ratio | (O.D) |
| 10 | 2 | 5:1 | 0.39 |
| 5 | 1* | 5:1 | 0.42* |
| 2.5 | 0.5 | 5:1 | 0.07 |
| 0 | 0 | Blank | 0.07 |

TABLE 4

Identifying NOHA antigen lowest concentration range for ELISA assay.

| In well concentration after 1:1 mix of reagents | | Observed/calculated NOHA |
|---|---|---|
| NOHA (ng/ml) | mAB (ng/ml) | (ng/ml) |
| 20 | 1 | 19.1 |
| 10 | 1 | 9.7 |
| 4 | 1 | 3.87 |
| 1 | 1 | 0.94 |
| 0.4 | 1 | 0.37 |
| 0.2 | 1 | 0.18 |
| 0.1 | 1 | 0.09 |
| 0.06* | 1 | 0.057* |
| 0.05 | 1 | NA |
| 0 | 1 | NA |
| 0 | 0 | NA |

*represents the lowest effective NOHA antigen concentration, that is quantifiable using 1 ng/ml monoclonal NOHA antibody (mAB).
NA represents not available/calculatable data.

TABLE 5

Measurement of inter-day precision of ELISA Assay. No statistically significant difference between theoretical and observed values

| Theoretical NOHA concentration (ng/ml) + 5 ng/ml mAB | Number of replicated (n) | Calculated/observed (ng/ml) Mean ± St.Dev | % Covariance |
|---|---|---|---|
| 50 | 4 | 50.1 ± 1.8 | 3.5 |
| 20 | 4 | 20.4 ± 1.7 | 8.1 |
| 10 | 4 | 9.8 ± 1.3 | 12.6 |

TABLE 6

Measurement of inter-day precision of ELISA Assay. No statistically significant difference exists between theoretical and observed values

| Theoretical NOHA concentration (ng/ml) + 5 ng/ml mAB | Number of replicated (n) | Calculated/observed (ng/ml) Mean ± St.Dev | % Covariance |
|---|---|---|---|
| 50 | 4 | 49.8 ± 1.2 | 2.5 |
| 20 | 4 | 19.9 ± 0.7 | 3.7 |
| 10 | 4 | 10.1 ± 0.7 | 7.2 |

TABLE 7

Measurement of Selectivity for NOHA measurement by ELISA assay using monoclonal NOHA antibody (mAB).

| | | | | | | |
|---|---|---|---|---|---|---|
| Theoretical NOHA concentration (ng/ml) + 5 ng/ml mAB | 20 | 20 | 20 | 20 | 20 | 20 |
| Spiked Cationic amino acids | L-Arginine | D-Arginine | L-Lysine | D-Lysine | L-Citrulline | L-Ornithine |
| Spiked Cationic amino acids concentration (ng/ml) | 50 | 50 | 50 | 50 | 50 | 50 |
| Number of replicates (n) | 4 | 4 | 4 | 4 | 4 | 4 |
| Calculated/observed (ng/ml) Mean ± St. Dev | 20.1 ± 0.9* | 19.7 ± 0.8* | 20.1 ± 0.8* | 19.9 ± 0.8* | 20.1 ± 0.8* | 20.1 ± 0.8* |
| % Covariance | 8.6 | 7.2 | 8.2 | 7.4 | 8.3 | 8.4 |

*represents selectivity of mAB to only NOHA, in the presence of other cationic amino acids, irrespective of their enantiomeric state (i.e. D-form versus L-form).

TABLE 8

Sample dilution recovery precision of the ELISA assay using NOHA monoclonal antibody for NOHA measurement No statistically significant difference exists between theoretical and observed values

| Theoretical NOHA concentration (ng/ml) + 5 ng/ml mAB | Dilution fold | Number of replicates | Expected NOHA (ng/ml) | Calculated/observed (ng/ml) Mean ± St. Dev | % Covariance |
|---|---|---|---|---|---|
| 50 | 2 | 4 | 25 | 24.9 ± 1.1 | 4.4 |
| 20 | 2 | 4 | 10 | 9.8 ± 0.9 | 9.7 |
| 10 | 2 | 4 | 5 | 5.3 ± 0.6 | 11.2 |

TABLE 9

Spiked sample recovery precision of the ELISA assay using NOHA monoclonal antibody for NOHA measurement. No statistically significant difference exists between theoretical and observed values

| Theoretical NOHA concentration (ng/ml) + 5 ng/ml mAB | Spiked NOHA (ng/ml) | Number of replicates | Expected NOHA (ng/ml) | Calculated/observed (ng/ml) Mean ± St. Dev | % Covariance |
|---|---|---|---|---|---|
| 50 | 50 | 4 | 100 | 98.4 ± 5.1 | 5.2 |
| 20 | 30 | 4 | 50 | 50.6 ± 3.4 | 6.7 |
| 10 | 15 | 4 | 25 | 24.6 ± 1.3 | 5.4 |

TABLE 10

Comparative analysis of NOHA quantification between ELISA and LC-MS methods.

| NOHA (ng/ml) ± 5 ng/ml mAB | Number of replicates | Calculated/observed (ng/ml) Mean ± St. Dev | | % Covariance | |
|---|---|---|---|---|---|
| | | By ELISA | By LC-MS | By ELISA | By LC-MS |
| 100 | 4 | 98.6 ± 5.3# | 99.5 ± 5.6 | 5.4 | 5.7 |
| 50 | 4 | 50.4 ± 3.9# | 50.2 ± 4.3 | 7.8 | 8.5 |

No statistically significant difference exists between theoretical and observed values;
represents comparable NOHA measurements between ELISA and LC-MS assays.

In reference to FIG. 7, the NOHA antigen of 150-0 ng/ml with 5 ng/ml monoclonal NOHA antibody (mAB) was used. The O.D. values (Y-axis) was plotted against the log NOHA antigen standard concentrations (X-axis), as an XY scatter plot. A polynomial order-2 trendline and R-squared confidence value were added.

Figure 8:
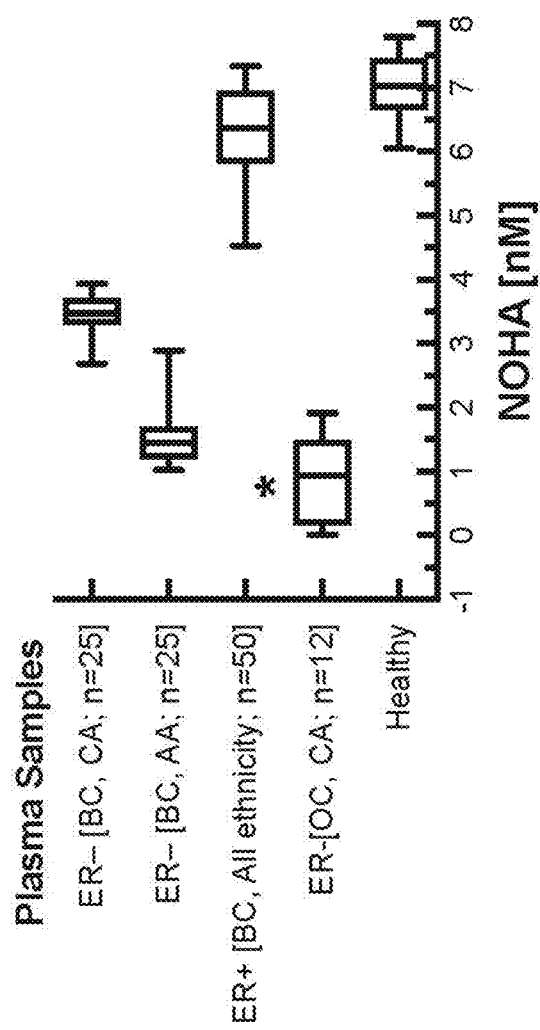
FIG. 8 is a graph of plasma NOHA protein measured by ELISA in ER− and ER+ ovarian and breast cancer patients by ELISA While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

In reference to FIG. 8, plasma from patients with low-grade, stage-1, ovarian cancer (OC) or breast cancer (BC), who are either estrogen-negative (ER−) or estrogen hormone-receptor positive (ER+) were tested for NOHA, by ELISA assay. *, represents significant difference between ER− BC and ER− OC patients of Caucasian (CA) ethnic origin. AA represents African American patients.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A method of monitoring breast cancer or ovarian cancer in a subject, the method comprising:
    contacting a first and a second sample derived from the subject with an antibody or an antigen-binding fragment thereof that specifically binds N$^w$-hydroxy-L-Arginine (NOHA), wherein the second sample is obtained from the subject subsequent to when the first sample is obtained from the subject;
    detecting binding of NOHA to the antibody or the antigen-binding fragment thereof in the first and second samples, and
    comparing the detected binding in the first and second samples, wherein a change in the amount of NOHA in the second sample relative to the first is indicative of change in disease status in the subject
    (a) wherein the antibody or the antigen-binding fragment thereof comprises a heavy chain variable region (VH1) comprising three CDRs, which include CDR1 comprising amino acids SGYYWN (SEQ ID NO: 14), CDR2 comprising amino acids YTNYDGSNNYNPSLKN (SEQ ID NO: 16), and CDR3 comprising amino acids PYLDY (SEQ ID NO: 18), and a light chain variable region (VL1) comprising three CDRs, which include CDR1 comprising amino acids SVSSSISSSYLH (SEQ ID NO: 46), CDR2 comprising amino acids GTSNLAS (SEQ ID NO: 48), and CDR3 comprising amino acids QQWSSYPLT (SEQ ID NO: 50); or
    (b) wherein the antibody or the antigen-binding fragment thereof comprises a heavy chain variable region (VH2) comprising three CDRs, which include CDR1 comprising amino acids SNVMH (SEQ ID NO: 30), CDR2 comprising amino acids YINPYNDGTKYNEKFKG (SEQ ID NO: 32), and CDR3 comprising amino acids HFDYYGRGYAVDY (SEQ ID NO: 34), and a light chain variable region (VL2) comprising three CDRs, which include CDR1 comprising amino acids SASQDISNYLN (SEQ ID NO: 62), CDR2 comprising amino acids YTSSLHS (SEQ ID NO: 64), and CDR3 comprising amino acids LQYSKLPWT (SEQ ID NO: 66).

2. The method of claim 1, wherein the antibody or the antigen-binding fragment thereof comprises a heavy chain variable region (VH1) comprising amino acid sequence:

MMVLSLLYLLTAIPGILSDVQLQESGPGLVKP-SQSLSLTCSVTGYSITSGYYWNWIRQFP GNKLEWMGYTNYDGSNNYNPSLKNRISI-TRDTSKNQFFLKLNSVTTEDTGTYYCAGPYL DYWGQGTTLTVSS (SEQ ID NO: 6); and a light chain variable region (VL1) comprising amino acid sequence MDFQVQIISFMLISVTVMLSSGEIVLTQSPAL-MAASPGEKVTITCSVSSSISSSYLHWYQQ RSETSPKPWIYGTSNLASGVPVRFSGNGSGTSYSL-TISSMEAEDAATYYCQQWSSYPLTF GGGTKLEIK (SEQ ID NO: 38).

3. The method of claim 1, wherein the antibody or the antigen-binding fragment thereof comprises a heavy chain variable region (VH2) comprising amino acid sequence MEWSGIFLFLLSGTAGVHFE-VQLQQSGPELVKPGASVKMSCK-ASGYKFTSNVMHW VKQKPGQGLEWIGY-INPYNDGTKYNEKFKGKATLTSDKSSSTAYM-ELSSLTSEDSA VYYCGRHFDYYGRG-YAVDYWGQGTSVTVSS (SEQ ID NO: 22); and a light chain variable region (VL2) comprising amino acid sequence MVS-SAQFLGLLLLCFQGTRCDIQMTQTTSSL-SASLGDRVTISCSASQDISNYLNW YQRKPDGTVKLLIYYTSSLHSGVPSRFSGSG-SGTDYSLTISNLEPEDIATYYCLQY SKLPWTFGGGTKLEIK (SEQ ID NO: 54).

4. The method of claim 1, wherein the detecting is by immunoassay.

5. An antibody or an antigen-binding fragment thereof that specifically binds $N^w$-hydroxy-L-Arginine (NOHA), wherein the antibody or the antigen-binding fragment thereof comprises (a) a heavy chain variable region (VH1) comprising three CDRs, which include CDR1 comprising amino acids SGYYWN (SEQ ID NO: 14), CDR2 comprising amino acids YTNYDGSNNYNPSLKN (SEQ ID NO: 16), and CDR3 comprising amino acids PYLDY (SEQ ID NO: 18), and a light chain variable region (VL1) comprising three CDRs, which include CDR1 comprising amino acids SVSSSISSSYLH (SEQ ID NO: 46), CDR2 comprising amino acids GTSNLAS (SEQ ID NO: 48), and CDR3 comprising amino acids QQWSSYPLT (SEQ ID NO: 50); or (b) a heavy chain variable region (VH2) comprising three CDRs, which include CDR1 comprising amino acids SNVMH (SEQ ID NO: 30), CDR2 comprising amino acids YINPYNDGTKYNEKFKG (SEQ ID NO: 32), and CDR3 comprising amino acids HFDYYGRG-YAVDY (SEQ ID NO: 34) and a light chain variable region (VL2) comprising three CDRs, which include CDR1 comprising amino acids SASQDISNYLN (SEQ ID NO: 62); CDR2 comprising amino acids YTSSLHS (SEQ ID NO: 64), and CDR3 comprising amino acids LQYSKLPWT (SEQ ID NO: 66).

6. The antibody or the antigen-binding fragment thereof of claim 5, wherein the antibody or the antigen-binding fragment thereof comprises a heavy chain variable region (VH1) comprising amino acid sequence MMVLSLLYLL-TAIPGILSDVQLQESGPGLVKP-SQSLSLTCSVTGYSITSGYYWNWIRQFP GNKLEWMGYTNYDGSNNYNPSLKNRISI-TRDTSKNQFFLKLNSVTTEDTGTYYCAGPYL DYWGQGTTLTVSS (SEQ ID NO: 6); and a light chain variable region (VL1) comprising amino acid sequence MDFQVQIISFMLISVTVMLSSGEIVLTQSPAL-MAASPGEKVTITCSVSSSISSSYLHWYQQ RSETSPKP-WIYGTSNLASGVPVRFSGNGSGTSYSLTISSMEAE-DAATYYCQQWSSYPLTF GGGTKLEIK (SEQ ID NO: 38).

7. The antibody or the antigen-binding fragment thereof of claim 5, wherein the antibody or the antigen-binding fragment comprise a heavy chain variable region (VH2) comprising amino acid sequence MEWSGI-FLFLLSGTAGVHFEVQLQQSGPELVKPGASVKMSCK-ASGYKFTSNVMHWVK QKPGQGLEWIGY-INPYNDGTKYNEKFKGKATLTSDKSSSTAYMELSSL-TSEDSAVYYCG RHFDYYGRG-YAVDYWGQGTSVTVSS (SEQ ID NO: 22); and a light chain variable region (VL2) comprising amino acid sequence MVS-SAQFLGLLLLCFQGTRCDIQMTQTTSSL-SASLGDRVTISCSASQDISNYLNWYQRKP DGTVKLLIYYTSSLHSGVPSRFSGSGSGTDYSLTISN-LEPEDIATYYCLQYSKLPWTFGGG TKLEIK (SEQ ID NO: 54).

8. The method of claim 2, wherein the heavy chain variable region (VH1) is encoded by the polynucleotide sequence of SEQ ID NO: 4 and the light chain variable region (VL1) is encoded by the polynucleotide sequence of SEQ ID NO: 36.

9. The method of claim 3, wherein the heavy chain variable region (VH2) is encoded by the polynucleotide sequence of SEQ ID NO: 20 and the light chain variable region (VL2) is encoded by the polynucleotide sequence of SEQ ID NO: 52.

10. The method of claim 6, wherein the heavy chain variable region (VH1) is encoded by the polynucleotide sequence of SEQ ID NO: 4 and the light chain variable region (VL1) is encoded by the polynucleotide sequence of SEQ ID NO: 36.

11. The method of claim 7, wherein the heavy chain variable region (VH2) is encoded by the polynucleotide sequence of SEQ ID NO: 20 and the light chain variable region (VL2) is encoded by the polynucleotide sequence of SEQ ID NO: 52.

\* \* \* \* \*

SEQUENCE LISTING

<160> NUMBER OF SEQ ID NOS: 66

<210> SEQ ID NO 1
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 1

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ala Ser Phe Asn Arg Asn Glu Cys
            100                 105

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Thr Ser Thr Ser
1               5

<210> SEQ ID NO 3

<400> SEQUENCE: 3

000

<210> SEQ ID NO 4
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgatggtgt taagtcttct gtacctgttg acagccattc ctggtatcct gtctgatgta      60
cagcttcagg agtcaggacc tggcctcgtg aaaccttctc agtctctgtc tctcacctgc     120
tctgtcactg gctactccat caccagtggt tattactgga actggatccg gcagtttcca     180
ggaaacaaac tggaatggat gggctacaca aactacgacg tagcaataa ctacaaccca      240 tctctcaaaa atcgaatctc catcactcgt gacacatcta agaaccagtt tttcctgaag     300
ttgaattctg tgactactga ggacacaggt acatattact gtgcgggacc ctaccttgac     360
tactggggcc aaggcaccac tctcacagtc tcctca                               396

<210> SEQ ID NO 5

<400> SEQUENCE: 5

000

<210> SEQ ID NO 6
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Met Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Tyr Trp Asn Trp Ile Arg Gln Phe Pro Gly Asn Lys Leu
    50                  55                  60

Glu Trp Met Gly Tyr Thr Asn Tyr Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Thr Gly Thr Tyr
            100                 105                 110

Tyr Cys Ala Gly Pro Tyr Leu Asp Tyr Trp Gly Gln Gly Thr Thr Leu
        115                 120                 125

Thr Val Ser Ser
    130

<210> SEQ ID NO 7

<400> SEQUENCE: 7

000

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agtggttatt actggaac                                                 18

<210> SEQ ID NO 9

<400> SEQUENCE: 9

000

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tacacaaact acgacggtag caataactac aacccatctc tcaaaaat               48

<210> SEQ ID NO 11

<400> SEQUENCE: 11

000

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ccctaccttg actac                                                          15

<210> SEQ ID NO 13

<400> SEQUENCE: 13

000

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Gly Tyr Tyr Trp Asn
1               5

<210> SEQ ID NO 15

<400> SEQUENCE: 15

000

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Thr Asn Tyr Asp Gly Ser Asn Asn Tyr Asn Pro Ser Leu Lys Asn
1               5                   10                  15

<210> SEQ ID NO 17

<400> SEQUENCE: 17

000

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Tyr Leu Asp Tyr
1               5

<210> SEQ ID NO 19

<400> SEQUENCE: 19

000

<210> SEQ ID NO 20
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggaatgga gcgggatctt tctctttctc ctgtcaggaa ctgcaggtgt ccactttgag    60
gtccagctgc agcagtctgg acctgagctg gtaaagcctg gggcttcagt gaagatgtcc   120
tgcaaggctt ctggatacaa attcactagc aatgttatgc actgggtgaa gcagaagcct   180
gggcagggcc ttgagtggat tggatatatt aatccttaca atgatggtac taagtacaat   240
gagaagttca aggcaaggc cacactgact tcagacaaat cctccagcac agcctacatg   300
gagctcagca gcctgacctc tgaggactct gcggtctatt actgtggaag acatttgat   360 tactacggta ggggctacgc tgtggactac tggggtcaag gaacctcagt caccgtctcc   420
tca                                                                  423

<210> SEQ ID NO 21

<400> SEQUENCE: 21

000

<210> SEQ ID NO 22
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Glu Trp Ser Gly Ile Phe Leu Phe Leu Leu Ser Gly Thr Ala Gly
1               5                   10                  15

Val His Phe Glu Val Gln Leu Gln Gln Ser Gly Pro Glu Leu Val Lys
                20                  25                  30

Pro Gly Ala Ser Val Lys Met Ser Cys Lys Ala Ser Gly Tyr Lys Phe
            35                  40                  45

Thr Ser Asn Val Met His Trp Val Lys Gln Lys Pro Gly Gln Gly Leu
        50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Gly Arg His Phe Asp Tyr Tyr Gly Arg Gly Tyr Ala Val
            115                 120                 125

Asp Tyr Trp Gly Gln Gly Thr Ser Val Thr Val Ser Ser
    130                 135                 140

<210> SEQ ID NO 23

<400> SEQUENCE: 23

000

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agcaatgtta tgcac                                                      15

<210> SEQ ID NO 25

<400> SEQUENCE: 25

000

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tatattaatc cttacaatga tggtactaag tacaatgaga agttcaaagg c               51

<210> SEQ ID NO 27

<400> SEQUENCE: 27

000

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cattttgatt actacggtag gggctacgct gtggactac                             39

<210> SEQ ID NO 29

<400> SEQUENCE: 29

000

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Asn Val Met His
1               5

<210> SEQ ID NO 31

<400> SEQUENCE: 31

000

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Tyr Ile Asn Pro Tyr Asn Asp Gly Thr Lys Tyr Asn Glu Lys Phe Lys
1               5                   10                  15

Gly

<210> SEQ ID NO 33

<400> SEQUENCE: 33

000

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Phe Asp Tyr Tyr Gly Arg Gly Tyr Ala Val Asp Tyr
1               5                   10

<210> SEQ ID NO 35

<400> SEQUENCE: 35

000

<210> SEQ ID NO 36
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36 atggatttc aggtgcagat tatcagcttc atgctaatca gtgtcacagt catgttgtcc      60
agtggagaaa ttgtgctcac acagtctcca gcactcatgg ctgcatctcc aggggagaag    120
gtcaccatca cctgcagtgt cagctcaagt ataagttcca gctacttaca ctggtaccag    180
cagaggtcag aaacctcccc caaaccctgg atttatggca catccaacct ggcttctgga    240
gtccctgttc gcttcagtgg caatggatct gggacctctt attctctcac aataagcagc    300
atggaggctg aagatgctgc cactattac tgtcaacagt ggagtagtta cccactcacg      360

-continued ttcggagggg ggaccaagct ggaaataaaa        390

<210> SEQ ID NO 37

<400> SEQUENCE: 37

000

<210> SEQ ID NO 38
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Asp Phe Gln Val Gln Ile Ile Ser Phe Met Leu Ile Ser Val Thr
1               5                   10                  15

Val Met Leu Ser Ser Gly Glu Ile Val Leu Thr Gln Ser Pro Ala Leu
            20                  25                  30

Met Ala Ala Ser Pro Gly Glu Lys Val Thr Ile Thr Cys Ser Val Ser
        35                  40                  45

Ser Ser Ile Ser Ser Ser Tyr Leu His Trp Tyr Gln Gln Arg Ser Glu
    50                  55                  60

Thr Ser Pro Lys Pro Trp Ile Tyr Gly Thr Ser Asn Leu Ala Ser Gly
65                  70                  75                  80

Val Pro Val Arg Phe Ser Gly Asn Gly Ser Gly Thr Ser Tyr Ser Leu
                85                  90                  95

Thr Ile Ser Ser Met Glu Ala Glu Asp Ala Ala Thr Tyr Tyr Cys Gln
            100                 105                 110

Gln Trp Ser Ser Tyr Pro Leu Thr Phe Gly Gly Gly Thr Lys Leu Glu
        115                 120                 125

Ile Lys
    130

<210> SEQ ID NO 39

<400> SEQUENCE: 39

000

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agtgtcagct caagtataag ttccagctac ttacac        36

<210> SEQ ID NO 41

<400> SEQUENCE: 41

000

<210> SEQ ID NO 42
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 42
ggcacatcca acctggcttc t                                              21

<210> SEQ ID NO 43

<400> SEQUENCE: 43

000

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
caacagtgga gtagttaccc actcacg                                        27

<210> SEQ ID NO 45

<400> SEQUENCE: 45

000

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Val Ser Ser Ser Ile Ser Ser Ser Tyr Leu His
1               5                   10

<210> SEQ ID NO 47

<400> SEQUENCE: 47

000

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Thr Ser Asn Leu Ala Ser
1               5

<210> SEQ ID NO 49

<400> SEQUENCE: 49

000

<210> SEQ ID NO 50
```

<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gln Gln Trp Ser Ser Tyr Pro Leu Thr
1               5

<210> SEQ ID NO 51

<400> SEQUENCE: 51

000

<210> SEQ ID NO 52
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
atggtgtcct cagctcagtt ccttggtctc ctgttgctct gttttcaagg taccagatgt    60
gatatccaga tgacacagac tacatcctcc ctgtctgcct ctctgggaga cagagtcacc   120
atcagttgca gtgcaagtca ggacattagc aattatttaa actggtatca acggaaacca   180
gatggaactg ttaaactcct gatctattac acatcaagtt tacactcagg agtcccatca   240
aggttcagtg gcagtgggtc tgggacagat tattctctca ccatcagcaa cctggaacct   300
gaagatattg ccacttacta ttgtctgcag tatagtaagc ttccgtggac gttcggtgga   360
ggcaccaagc tggaaatcaa a                                             381
```

<210> SEQ ID NO 53

<400> SEQUENCE: 53

000

<210> SEQ ID NO 54
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Met Val Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Ser Ala Ser Gln Asp
        35                  40                  45

Ile Ser Asn Tyr Leu Asn Trp Tyr Gln Arg Lys Pro Asp Gly Thr Val
    50                  55                  60

Lys Leu Leu Ile Tyr Tyr Thr Ser Ser Leu His Ser Gly Val Pro Ser
65                  70                  75                  80

Arg Phe Ser Gly Ser Gly Ser Gly Thr Asp Tyr Ser Leu Thr Ile Ser
                85                  90                  95

```
Asn Leu Glu Pro Glu Asp Ile Ala Thr Tyr Tyr Cys Leu Gln Tyr Ser
            100                 105                 110

Lys Leu Pro Trp Thr Phe Gly Gly Gly Thr Lys Leu Glu Ile Lys
        115                 120                 125
```

<210> SEQ ID NO 55

<400> SEQUENCE: 55

000

<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
agtgcaagtc aggacattag caattattta aac                                   33

<210> SEQ ID NO 57

<400> SEQUENCE: 57

000

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tacacatcaa gtttacactc a                                                21

<210> SEQ ID NO 59

<400> SEQUENCE: 59

000

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ctgcagtata gtaagcttcc gtggacg                                          27

<210> SEQ ID NO 61

<400> SEQUENCE: 61

000

<210> SEQ ID NO 62
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 62

Ser Ala Ser Gln Asp Ile Ser Asn Tyr Leu Asn
1               5                   10

<210> SEQ ID NO 63

<400> SEQUENCE: 63

000

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Tyr Thr Ser Ser Leu His Ser
1               5

<210> SEQ ID NO 65

<400> SEQUENCE: 65

000

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Leu Gln Tyr Ser Lys Leu Pro Trp Thr
1               5
```